(12) United States Patent
Serra

(10) Patent No.: US 8,916,164 B2
(45) Date of Patent: Dec. 23, 2014

(54) METHODS OF ENHANCING ADJUVATICITY OF VACCINE COMPOSITIONS

(75) Inventor: Vincent Serra, Bondoufle (FR)

(73) Assignee: ABIVAX, Paris (FR)

( * ) Notice: Subject to any disclaimer, the term of this patent is extended or adjusted under 35 U.S.C. 154(b) by 236 days.

(21) Appl. No.: 12/675,595

(22) PCT Filed: Aug. 28, 2008

(86) PCT No.: PCT/IB2008/003016
§ 371 (c)(1),
(2), (4) Date: Jul. 12, 2010

(87) PCT Pub. No.: WO2010/023498
PCT Pub. Date: Mar. 4, 2010

(65) Prior Publication Data
US 2010/0285042 A1    Nov. 11, 2010

Related U.S. Application Data

(60) Provisional application No. 60/968,731, filed on Aug. 29, 2007.

(51) Int. Cl.
| A61K 39/00 | (2006.01) |
| A61K 38/17 | (2006.01) |
| C07H 15/04 | (2006.01) |
| A61K 39/39 | (2006.01) |

(52) U.S. Cl.
CPC ....... *A61K 39/39* (2013.01); *A61K 2039/55511* (2013.01)
USPC .................................. 424/184.1; 424/278.1

(58) Field of Classification Search
None
See application file for complete search history.

(56) References Cited

U.S. PATENT DOCUMENTS

| 5,242,800 | A | 9/1993 | Jimenez et al. |
| 5,604,207 | A | 2/1997 | DeFrees et al. |
| 5,767,092 | A | 6/1998 | Koezuka et al. |
| 5,780,441 | A | 7/1998 | Higa et al. |
| 5,785,975 | A | 7/1998 | Parikh |
| 5,849,716 | A | 12/1998 | Akimoto et al. |
| 5,936,076 | A | 8/1999 | Higa et al. |
| 5,958,426 | A | 9/1999 | Moreau et al. |
| 6,054,433 | A | 4/2000 | Elias et al. |
| 6,071,884 | A | 6/2000 | Koezuka et al. |
| 6,417,167 | B1 | 7/2002 | Maruyama et al. |
| 6,531,453 | B1 | 3/2003 | Taniguchi et al. |
| 6,610,835 | B1 | 8/2003 | Liotta et al. |
| 6,635,622 | B2 | 10/2003 | Tomiyama et al. |
| 6,747,010 | B2 | 6/2004 | Taniguchi et al. |
| 7,273,852 | B2 | 9/2007 | Tsuji et al. |
| 7,273,853 | B2 | 9/2007 | Or et al. |
| 7,645,873 | B2 | 1/2010 | Savage et al. |
| 7,989,423 | B2 | 8/2011 | Savage et al. |
| 8,207,135 | B2 * | 6/2012 | Serra .............. 514/25 |
| 8,642,565 | B2 * | 2/2014 | Serra .............. 514/25 |
| 2002/0115624 | A1 | 8/2002 | Behar et al. |
| 2003/0139351 | A1 | 7/2003 | Taniguchi et al. |
| 2003/0153514 | A1 | 8/2003 | Yagita |
| 2003/0157113 | A1 | 8/2003 | Terman |
| 2003/0157135 | A1 | 8/2003 | Tsuji et al. |
| 2004/0127429 | A1 | 7/2004 | Tsuji |
| 2004/0166554 | A1 | 8/2004 | Chamoles |
| 2004/0266726 | A1 | 12/2004 | Yagita |
| 2005/0192248 | A1 | 9/2005 | Tsuji et al. |
| 2005/0222048 | A1 | 10/2005 | Tsuji et al. |
| 2006/0019246 | A1 | 1/2006 | Tsuji et al. |
| 2006/0073118 | A1 | 4/2006 | Bendelac et al. |
| 2006/0211856 | A1 | 9/2006 | Tsuji et al. |
| 2008/0095787 | A1 | 4/2008 | Teyton |
| 2008/0279894 | A1 | 11/2008 | Teyton et al. |
| 2009/0047299 | A1 | 2/2009 | Savage |
| 2009/0162385 | A1 | 6/2009 | Serra |

FOREIGN PATENT DOCUMENTS

| EP | 0988860 | 3/2000 |
| EP | 1016409 | 7/2000 |
| WO | WO 99/33475 | 7/1999 |
| WO | WO 03/009812 | 2/2003 |
| WO | WO 03/018039 | 3/2003 |
| WO | WO 03/105769 | 12/2003 |
| WO | WO 2004/094444 | 11/2004 |
| WO | WO 2005/000348 | 1/2005 |
| WO | WO 2005/102049 | 11/2005 |
| WO | WO 2006/026389 | 3/2006 |
| WO | WO 2006/029010 | 3/2006 |
| WO | WO 2006/083671 | 8/2006 |
| WO | WO 2007/007946 | 1/2007 |
| WO | WO 2007/050668 | 5/2007 |
| WO | WO 2007/118234 | 10/2007 |

(Continued)

OTHER PUBLICATIONS

Ando et al., "Solid-phase capture-release strategy applied to oligosaccharide synthesis on a soluble polymer support," *Agnew. Chem. Int. Ed.* (2001) 40:4725-4728.

Beaudoin, L. et al., "NKT cells inhibit the onset of diabetes by impairing the development of pathogenic T cells specific for pancreatic beta cells," *Immunity* (2002) 17:725-736.

Bendelac et al., "Increased interleukin 4 and immunoglobulin E production in transgenic mice overexpressing NKI T cells," *J. Exp. Med.* (1996) 184: 1285-1293.

Bendelac, A. et al., "Autoreactivity by design: innate B and T lymphocytes," *Natur. Rev. Immunol.* (2001) 1:177-186.

Bendelac, A. et al., "The biology of NKT cells," *Ann. Rev. Immunol.* (2007) 25:297-336.

Bendelac, A., "Nondeletional pathways for the development of autoreactive thymocytes," *Nat. Immunol.* (2004) 5:557-558.

(Continued)

*Primary Examiner* — Yunsoo Kim
(74) *Attorney, Agent, or Firm* — Merchant & Gould P.C.

(57) ABSTRACT

The immunogenicity of vaccines is enhanced by co-administering a synthetic glycolipid, designated PBS-57, with the vaccine. PBS-57 has the ability to stimulate both a cell-mediated and humoral immune response. Co-administration of PBS-57 with a vaccine may be used in methods to stimulate one or more of a humoral immune response, a CD4+ T cell response, and a CD8+ cytotoxic T cell response.

21 Claims, 16 Drawing Sheets

(56) References Cited

FOREIGN PATENT DOCUMENTS

| | | |
|---|---|---|
| WO | WO 2007/126163 | 11/2007 |
| WO | WO 2008/005824 | 1/2008 |
| WO | WO 2008/080926 | 7/2008 |
| WO | WO 2008/082156 | 7/2008 |
| WO | WO 2009/060086 | 5/2009 |
| WO | WO 2010/040710 | 4/2010 |

OTHER PUBLICATIONS

Benlagha, K. et al., "In vivo identification of glycolipid antigen-specific T cells using fluorescent CD1d tetramers," *J. Exp. Med.* (2000) 191:1895-1903.
Brigl et al., "Mechanism of CD1d-restricted natural killer T cell activation during microbial infection," *Nat. Immunol.* (2003) 4: 1230-1237.
Brigl et al., "T cell function and antigen presentation," *Annu. Rev. Immunol.* (2004) 22: 817-890.
Brossay, L. et al., "Cutting edge: structural requirements for galactosylceramide recognition by CD1-restricted NK T cells," *J. Immunol.* (1998) 161(10):5124-5128.
Brutkiewicz et al., "CD1d-mediated antigen presentation to natural killer T (NKT) cells," *Critical Reviews in Immunology* (2003) 23: 403-419.
Brutkiewicz et al., "Natural killer T (NKT) cells and their role in antitumor immunity," *Critical Reviews in Oncology/Hematology* (2002) 41: 287-298.
Cantu et al., "The paradox of immune molecular recognition of alpha-galactosylceramide; low affinity, low specificity for CD1d, high affinity for alpha beta TCRs," *J. Immunol.* (2003) 170: 4673-4682.
Corey et al., "A new method for the synthesis of organic nitro compounds," *J. Am. Chem. Soc.* (1984) 106:3682-3683.
Daoudi, J-M. et al., "New bicyclam-galcer analogue conjugates: synthesis and in vitro anti-HIV activity," *Biorg. Med. Chem. Lett.* (2004) 14:495-498.
Dascher, C.C. et al., "CDI Antigen Presentation and Infectious Disease," *Contributions to Microbiology* (2003) 10:164-182.
Davis, N.J. et al., "Chemical Synthesis of Disaccharides Which are Partial Structures of the Glycosaminoglycan Heparan Sulfate," *J. Chem. Soc.* (1994) 1:359-368.
De Libero, G. et al., "Self glycosphingolipids: new antigens recognized by autoreactive T lymphocytes," *News Physiol. Sci.* (2003) 18:71-76.
Fischer, K. et al., "Mycobacterial phosphatidylinositol mannoside is a natural antigen for CD1d-restricted T cells," *Proc. Natl. Acad. Sci. USA* (2004) 101:10685-10690.
Fuji et al., "Antitumor of α-galactosylceramide (KRN7000) on spontaneous hepatic metastases requires endogenous interleukin 12 in the liver," *Clinical Cancer Research* vol. 6, No. 8 (2000) pp. 3380-3387.
Fujii et al., "Activation of natural killer T cells by alpha-galactosylceramide rapidly induces the full maturation of dendritic cells in vivo and thereby acts as an adjuvant for combined CD4 and CD8 T cell immunity to a coadministered protein," *J. Exp. Med.* (2003) 198:267-279.
Garrity, G.M. et al., Taxonomic Outline of the Procaryotic Genera, Bergey's Manual of Systematic Bacteriology, 2nd Edition (Apr. 2001).
Godfrey, D.I. et al., "Going both ways: immune regulation via CD1d-dependent NKT cells," *J. Clin. Invest.* (2004) 114(10):1379-1388.
Godfrey, D.I. et al., "The elusive NKT cell antigen—is the search over?" *Science* (2004) 306:1687-1688.
Goff, R.D. et al., "Effects of lipid chain lengths in alpha-galactosylceramides on cytokine release by natural killer T cells," *J. Am. Chem. Soc.* (2004) 126:13602-13603.
Goodman & Gilman's The Pharmacological Basis of Therapeutics, Tenth Edition, Hardman and Limbird, editors, The McGraw-Hill Companies, Inc., New York, (2001) 54-56.
Gui, M. et al., "TCR beta chain influences but does not solely control autoreactivity of V alpha 14J28IT cells," *J. Immunol.* (2001) 167(11):6239-6246.

Gumperz, J.E. et al., "Functional distinct subsets of CD1d-restricted natural killer T cells revealed by CD1d tetramer staining," *J. Exp. Med.* (2002) 195(5):625-636.
Gumperz, J.E. et al., "Murine CD1d-restricted T cell recognition of cellular lipids," *Immunity* (2000) 12:211-221.
Gupta, R.K. et al., "Adjuvants—a balance between toxicity and adjuvanticity," *Vaccine* (1993) 11(3):293-306.
Hashimoto, S. et al., "Glycosylation Using Glucopyranosyl Fluorides and Silicon-Based Catalysts, Solvent Dependency of the Stereoselection," *Tetrahedron Letters* (1984) 25:13:1379-1382.
Hayashi, M. et al., "Simple Synthesis of Glycosyl Fluorides," *Chem. Letters* (1984) 1747-1750.
Hermans, I.F. et al., "NKT cells enhance CD4+ and CD8+ T cell responses to soluble antigen in vivo through direct interaction with dendritic cells, " *J. Immunol.* (2003) 171:5140-5147.
Honey, K. et al., "Thymocyte expression of cathepsin L is essential for NKT cell development," *Nat. Immunol.* (2002) 3:1069-1074.
Iida, N. et al., "A sulfated glucosylceramide from rat kidney," *J. Biol. Chem.* (1989) 264(10):5974-5980.
Islam, I. et al., "Synthesis and antiviral activity of (2-((4-(3-((1-methylethyl)amino)-2-pyridyl)-1-piperazinyl)carbony)-1H-indo 1-5-yl) (BHAP) acylspingosine HIV reverse transcriptase inhibitors, " *Biorg. Chem.* (1995) 23(4):499-511.
Ismail, N. et al., "Overproduction of TNF-alpha b CD8+ type 1 cells and down-regulation of IFN-γ production by CD4+ Th 1 cells contribute to toxic shock-like syndrome in an animal model of fatal monocytotropic ehrlichiosis," *J. Immunol.* (2004) 172:1786-1800.
Kamijuku et al., "Mechanism of NKT cell activation by intranasal coadministration of alpha-galactosylceramdie, which can induce cross-protection against influenza viruses," *Mucosal Immunology* (2008) 1(3): 208-218. XP002558333.
Karadimitris, A. et al., "Human CD1d-glycolipid tetramers generated by in vitro oxidative refolding chromatography," *Proc. Natl. Acad. Sci. USA* (2001) 98(6):3294-3298.
Kawano, T. et al., "CD1d-restricted and TCR-mediated activation of Vα14 NKT cells by glycosylceramides," *Science* (1997) 278:1626-1629.
Khan, M. et al., "Syntheses and Antiinflammatory Activity of Some 6-aryl-2,3,4,5-tetrahydro-3-pyridazinones," *Indian J. Chem.* (2000) 39B:614-619.
Kinjo, Y. et al., "Recognition of bacterial glycosphingolipids by natural killer T cells," *Nature* (2005) 434:520-525.
Kitamura, H. et al., "The natural killer T (NKT) cell ligand alpha-galactosylceramide demonstrates its immunopotentiating effect by inducing interleukin (IL)-12 production by dendritic cells and IL-12 receptor expression on NKT cells," *J. Exp. Med.* (1999) 189:1121-1127.
Kopecky-Bromberg et al., "Alpha-C-galactosylceramide as an adjuvant for a live attenuated influenza virus vaccine," *Vaccine, Butterworth Scientific Guildford* (2009) 27 (28): 3766-3774. XP026134053.
Kronenberg, M., "Toward an understanding of NKT cell biology: progress and paradoxes," *Ann. Rev. Immunol* (2005) 23:877-900.
Lee, P.T. et al., "Testing the NKT cell hypothesis on human IDDM pathogenesis," *J. Clin. Invest.* (2002) 110(6):793-800.
Liu, Y. et al., "A modified alpha-galactosyl ceramide for staining and stimulating natural killer T cells," *J. Immun. Meth.* (2006) 312(1-2):34-39.
Long et al., "Synthesis and evaluation of stimulatory properties of Sphingomonadaceae glycolipds," *Nature Chemical Biology* (2007) 9: 559-564. XP002542183.
Matsuda, J.L. et al., "Tracking the response of natural killer T cells to a glycolipid antigen using CD1d tetramers," *J. Exp. Med.* (2000) 192(5):741-753.
Mattner, J. et al., "Exogenous and endogenous glycolipid antigens activate NKT cells during microbial infections," *Nature* (2005) 434:525-529.
Miyamoto, K. et al., "A Synthetic Glycolipid Prevents Autoimmune Encephalomyelitis by Inducing TH2 Bias of Natural Killer T Cells," *Nature* (2001) 413:531-534.
Morita, M. et al., "Structure-Activity Relationship of α-Galactosylceramides Against B16-Bearing Mice," *J. Med. Chem.* (1995) 38:2176-2187.

(56) References Cited

OTHER PUBLICATIONS

Nakagawa, R. et al., "Mechanisms of the Antimetastatic Effect in the Liver and of the Hepatocyte Injury Induced by α-Galactosylceramide in Mice," *J. Immun.* (2001) 166:11:6578-6584.

Pal, E. et al., "Costimulation-Dependent Modulation of Experimental Autoimmune Encephalomyelitis by Ligand Stimulation of Vα14 NK T Cells," *J. Immunol.* (2001) 166:662-668.

Park, S.H. et al., "CD1-restricted T-cell responses and microbial infection," *Nature* (2000) 406:788-792.

Park, S.H. et al., "The Mouse CD1d-restricted Repetoire is Dominated by a Few Autoreactive T cell Receptor Families," *J. Exp. Med.* (2001) 8:893-904.

Park, S.-H. et al., "Tissue-specific recognition of mouse CD1 molecules," *J. Immunol.* (1998) 160:3128-3134.

Petrovsky, N. et al., "Vaccine adjuvants: current state and future trends," *Immunol. Cell Biol.* (2004) 82:488-496.

Prigozy, T.I. et al., "Glycolipid antigen processing for presentation by CD1d molecules," *Science* (2001) 291:664-667.

Rock, K.L. et al., "Natural endogenous adjuvants," *Springer Semin. Immunopathol.* (2005) 26:231-24.

Sakai, T. et al., "Effects of α- and β-Galactosylated C2-Ceramides on the Immune System," *J. Med. Chem.* (1998) 41:650-652.

Sidobre, S. et al., "CD1d tetramers: a powerful tool for the analysis of glycolipid reactive T cells," *J. Immunol. Methods* (2002) 268:107-121.

Sinay, P. et al., "Synthesis of a 3-deoxy-L-iduronic acid containing heparin pentasaccharide to prode the conformation of the antithrombin III binding sequence," *Bioorganic and Medicinal Chemistry* (1998) 6: 1337-46.

Singh et al., "The natural killer T Cell ligand Alpha-Galactosylceramide protects mice against EAE by an IL-4 and IL-10-dependent mechanism," *FASEB J., Fed. Of Amer. Soc. For Exp. Bio* (2002) 16: A1043.

Singh, P.P. et al., "The Synthesis of 2,3,4,6,7-Penta-O-Methyl-D-glycero-L-manno-Heptose and 2,4,6,7-Tetra-O-Methyl-D-glycero-L-manno-Heptose," *Carbohydrate Res.* (1970) 12:261-266.

Smyth, M.J. et al., "NKT cells—conductors of tumor immunity?" *Curr. Opin. Immunol.* (2002) 14(2):165-171.

Smyth, M.J. et al., "NKT cells and tumor immunity—a double-edged sword," *Nature Immunology* (2001) 1:459-460.

Stanic A.K. et al., "Defective presentation of the CD1d1-restricted natural Va14Ja18 NKT lymphocyte antigen caused by Beta-D-glucosylceramide synthase deficiency," *Proc. Natl. Acad. Sci. USA* (2003) 100:1849-1854.

Supplementary Search Report of the European Patent Office for Application No. 03816701.1 dated Sep. 17, 2007.

Takikawa et al., "Diastereoselective Epoxidation of the Double Bond at C-4 of Sphinogosines to Provide Phytosphingosine Relatives such as α-Galactosylceramide KRN7000," *Tetrahedron* (1998) 54:3141-3150.

The Merck Manual, 16th Edition (1999): pp. 339-342 and 1488-1490.

United States Office Action for U.S. Appl. No. 10/550,165 mailed Oct. 27, 2008.

United States Office Action for U.S. Appl. No. 10/550,165 mailed Jan. 9, 2008.

United States Office Action for U.S. Appl. No. 10/550,165 mailed Jul. 20, 2007.

United States Office Action for U.S. Appl. No. 10/550,165 mailed Apr. 12, 2007.

United States Office Action for U.S. Appl. No. 11/218,906 dated Nov. 10, 2008 (8 pages).

United States Office Action for U.S. Appl. No. 11/771,128 dated Oct. 29, 2008 (14 pages).

United States Office Action for U.S. Appl. No. 12/625,048 mailed Sep. 29, 2010.

Van Der Vliet, H.J.J. et al., "Effects of α-galactosylceramide (KRN7000), interleukin-12 and interleukin-7 on phenotype and cytokine profile of human Vα24+Vβ11+T cells," *Immunology* (1999) 98:557-563.

Van Kaer, L., "Alpha-galactosylceramide therapy for autoimmune diseases: prospects and obstacles, " *Nat Rev. Immunol.* (2005) 5:31-42.

Vandommelen, S.L.H. et al., "Activation of natural killer (NK) T cells during murine cytomegalovirus infection enhances the antiviral response mediated by NK cells," *J. Virology* (2003) 77(3):1877-1884.

Vaultier, M. et al., "Reduction d'azides en amines primaires par une methode generale utilisant la reaction de staudinger," *Tetrahedron Letters* (1983) 24:763 (Not in English).

Wang, B. et al., "CD1-Restricted NK T Cells Protect Nonobese Diabetic Mice from Developing Diabetes," *J. Exp. Med.* (2001) 194:313-319.

Wang, F. et al., "Tuning of Binding Selectivity: Metal Control of Organic Guest Binding and Allosteric Perturbation of Fluorescent Metal Sensor," *J. Org. Chem.* (1999) 64:8922-8928.

Weber, G. et al., "Synthesis and Spectral Properties of a Hydrophobic Fluorescent Probe: 6-Propionyl-2-(dimethylamino) naphthalene," *Biochem.* (1979) 18:14:3075-3078.

Winau, F. et al., "Saposin C is required for lipid presentation by human CD1b," *Nat. Immunol.* (2004) 5:169-174.

Wu et al., "Bacterial glycolipids and analogs as antigen for CD1d-restricted NKT cells," *PNAS* (2005) 102(5):1351-1356.

Wu, D.Y. et al., "Cross-presentation of disialoganglioside GD3 to natural killer T cells," *J. Exp. Med.* (2003) 198:173-181.

Xia, C. et al., "Thio-isoglobotrihexosylceramide, an Agonist for activating invariant natural killer T cells," *Org. Lett.* (2006) 8(24):5493-5496.

Yamaguchi et al., "Enhancing Effects of (2S, 3S, 4R)-1-0-0 Alpha-D-Galactopyranosyl)-2- (N-Hexacosanoylamino)-1, 3, 4-Octadecanetriol (KRN7000) on Antigen-Presenting Function of Antigen-Presenting Cells and Antimetastatic Activity of KRN7000-Pretreated Antigen-Presenting Cells," *Oncology Research, Pergamon Press* (Jan. 1996) vol. 8, No. 10-11, pp. 399-407.

Yu, K.O.A. et al., "Modulation of CD1d-restricted NKT cell responses by using N-acyl variants of alpha-galactosylceramides," *Proc. Natl. Acad. Sci. USA* (2005) 102(9):3383-3388.

Zajonc, D.M. et al., "Structural basis for CD1d presentation of a sulfatide derived from myelin and its implications for autoimmunity," *J. Exp. Med.* (2005) 202(11):1517-1526.

Zajonc, D.M. et al., "Structure and function of a potent agonist for the semi-invariant natural killer T cell receptor," *Nat. Immunol.* (2005) 6:810-818.

Zhou et al., "Synthesis and NKT cell stimulating properties of fluorophore-and biotin-appended 6"-amino-6"-deoxy-galactosylceramides," *Org. Lett.* (2002) 4(8):1267-1270. XP003008968.

Zhou, D. et al., "Editing of CD1d-bound lipid antigens by endosomal lipid transfer proteins," *Science* (2004) 303:523-527.

Zhou, D. et al.,"Lysosomal glycosphingolipid recognition by NKT cells," *Science* (2004) 306:1786-1789.

Zhou, D., "The immunological function of iGb3," Curr. Prot. Pept. Sci. (2006) 7:325-333.

Supplemental European Search Report mailed Sep. 3, 2010 for EP 07760333.0.

International Search Report for Application No. PCT/EP2009/062894, 2010.

Written Opinion for Application No. PCT/EP2009/062894, 2010.

International Search Report for Application No. PCT/US2005/031407, 2005.

Written Opinion for Application No. PCT/US2005/031407, 2005.

International Search Report for International Application No. PCT/US2007/072451, 2007.

Written Opinion for International Application No. PCT/US2007/072451, 2007.

International Search Report for International Application No. PCT/US06/002781, 2006.

Written Opinion for International Application No. PCT/US06/002781, 2006.

International Search Report for International Application No. PCT/US07/66250, 2007.

Written Opinion for International Application No. PCT/US07/66250, 2007.

(56) References Cited

OTHER PUBLICATIONS

International Search Report for International Application No. PCT/US03/08530, 2003.

Written Opinion for International Application No. PCT/US03/08530, 2003.

Liu et al. "A modified α-galactosyl ceramide for staining and stimulating natural killer T cells." *Journal of Immunological Methods*. vol. 312. 2006. pp. 34-39.

Silk et al. "Utilizing the adjuvant properties of CD1d-dependent NK T cells in T cell-mediated immunotherapy." *Journal of Clinical Investigation*. vol. 114. No. 12. 2004. pp. 1810-1811.

Ko et al. "α-Galactosylceramide Can Act as a Nasal Vaccine Adjuvant Inducing Protective Immune Responses against Viral Infection and Tumor." *Journal of Immunology*. vol. 175. No. 5. 2005. pp. 3309-3317.

Zhou et al. "Synthesis and NKT Cell Stimulating Properties of Fluorophore- and Biotin-Appended 6"-Amino-6"-deoxy-galactosylceramides." *Organic Letters*. vol. 4. No. 8. 2002. pp. 1267-1270.

Moriya, T., "A New Immunological Mechanism for Malaria—The Involvement of NKT Cells-", *Infection, Inflammation, and Immunity*, vol. 32, No. 4, 2002, pp. 2-9. (English translation).

Yasushi et al., "Adjustment of the TH1/2 Balance by Means of Invariant NKT Cells", *Rinka Men'eki*, vol. 44, No. 6, 2005, pp. 682-688. (English translation).

\* cited by examiner

METHODS OF ENHANCING ADJUVATICITY OF VACCINE COMPOSITIONS

CROSS-REFERENCE TO RELATED APPLICATIONS

This application is a National Stage Application of PCT/IB2008/003016, filed 29 Aug. 2008, which claims benefit of U.S. Provisional Ser. No. 60/968,731, filed 29 Aug. 2007 and which applications are incorporated herein by Reference. To the extent appropriate, a claim of priority is made to each of the above disclosed applications.

INTRODUCTION

The fundamental purpose of a vaccine is to provide lasting immunity against a pathological condition. Ideally vaccines provide functionally active antibodies, elicit cell-mediated immunity, and activate T- and B-lymphocytes with highly specific reactivity as well as "memory" to provide protection against further encounters with a pathogen.

Adjuvants are vaccine additives which nonspecifically augment the immune response. The mechanism by which adjuvants enhance the immune system varies widely. Adjuvants may be classified as "immunomodulatory" or "antigen delivery systems." Immunomodulatory adjuvants prime the immune system by regulating the action of immune cells by altering lymphokine production. Antigen delivery systems, on the other hand, function to deliver the antigen to the appropriate immune cells. In addition, adjuvants may enhance the speed or duration of an immune response, modulate antibody avidity, specificity, isotype or subclass distribution, stimulate cell mediated immunity, promote mucosal immunity, or enhance the immune responses in immunologically immature or senescent individuals. Adjuvants can affect either the humoral or cell-mediated immune response, or a combination of both.

Immunomodulation refers to the ability of an adjuvant to alter the lymphokine response by activating differential subsets of immune cells. Two major subsets of CD4+ T lymphocytes, Th1 and Th2, play a major role in determining the immune response. Th1 responses typically induce complement fixing antibody and strong delayed-type hypersensitivity (DTH) reactions and are associated with γ-IFN, IL-2, and IL-12, while Th2 responses result in high circulating and secretory antibody levels and are associated with cytokines IL-4, IL-5, IL-6 and IL-10. Activation of Th1 cells also regulates the cellular immune response by activating the proliferation of cytotoxic CD8+ T cells and enhanced cytolysis of target cells.

Lipid species have been investigated for adjuvant properties. Unlike peptide antigens, lipids are processed and presented to the immune system by the CD1 family of β2 microglobulin-associated molecules. CD1 molecules have evolved to capture and process both foreign and self lipid antigens for display to particular subsets of T cells. The CD1 presentation pathway triggers both innate and adaptive immune response by activating two complementary CD1 restricted T cell subsets; natural killer T (NKT) cells that perform adjuvant functions; and non-NKT T-cells capable of helper or cytolytic functions. NKT cells express both natural killer (NK) cell surface markers and a conserved semi-invariant T-cell receptor (TCR), Vα24-Jα18/Vβ8 in mice and Vα24-Jα18/Vβ11 in humans. Accordingly, NKT cells play an important role in a number of immune functions, including antimicrobial responses, antitumor immunity, and regulation of the balance between tolerance and autoimmunity.

A number of natural and synthetic lipid molecules are processed by antigen-presenting cells and presented by CD1 molecules to NKT cells. The prototypical compound used to study NKT cell activation in vitro and in vivo is KRN7000, and α-galactosyceramide ("αGalCer") derived from marine sponge *Agelas mauritianus*. Additional compounds recently identified include isoglobotrihexosylceramide ("iGB3") which is an endogenous glycolipid and PBS-57, a modified 6"amino 6" deoxygalactosyceramide, as described in PCT Application PCT/US07/66250, the disclosure of which is incorporated herein by reference. These compounds activate NKT cells and upregulate cytokine responses in vitro. However, in the context of in vivo vaccinations, little is known regarding the effectiveness of lipid adjuvanticity for these compounds.

Few adjuvants have been approved for use in human vaccines due to toxic side effects. The most common adjuvants are aluminum and oil adjuvants, but they are known to induce side effects such as fever, headache, muscle aches and pains or rash. Other disadvantages include a strong local stimulation of the immune system leading to pain, redness, swelling or a small lump at the site of injection. Adjuvants also have complicated methods of vaccine preparation and may fail to increase immunogenicity of weak antigens. At present, the choice of adjuvants for human vaccination reflects a compromise between the requirement for adjuvanticity and an acceptable level of side effects. There is a need for new adjuvants with fewer side effects that still elicit long-lasting protective immunity.

SUMMARY OF INVENTION

The inventors have discovered that the addition of a synthetic glycolipid, designated PBS-57, to a vaccine preparation administered to a subject activates both a humoral and cellular immune response when administered to the subject. Accordingly, the invention provides methods of enhancing the immunogenicity of a vaccine in a subject, stimulating a humoral immune response, stimulating a CD4+ T cell response and stimulating a CD8+ cytotoxic T cell response in a subject by co-administering PBS-57 and a vaccine to a subject.

DETAILED DESCRIPTION OF SEVERAL EMBODIMENTS

Figure 1:
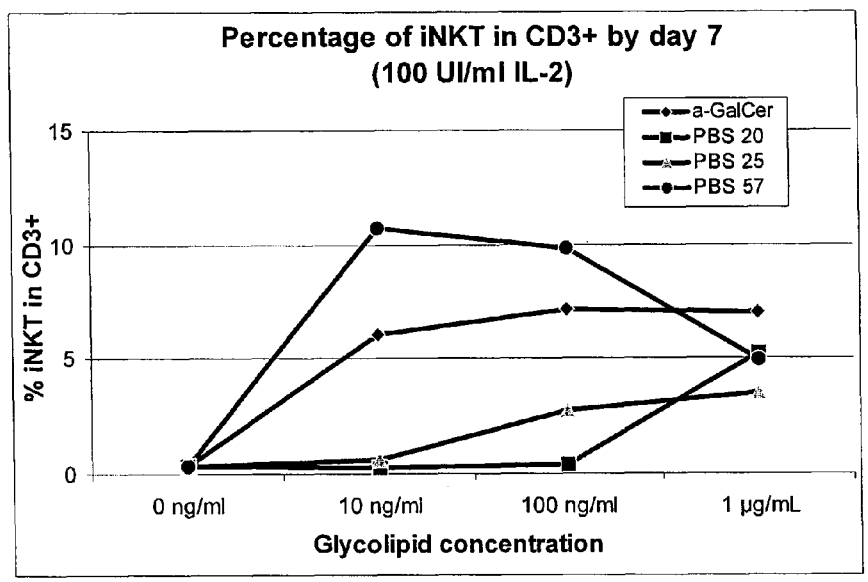
FIG. 1 is a graph showing the percentage of NKT cells on day 7 in a CD3+ T cell population of cultured peripheral blood lymphocytes (PBL) treated with various amounts of adjuvant glycolipids αGalCer, PBS20, PBS25 and PBS57.

Adjuvants enhance the immunogenicity of antigens in vaccine preparations in a variety of ways. In the case of toxins, a good humoral immune response is required. In the case of intracellular bacteria, a cell-mediated response, mediated mainly by cytotoxic T cells and Th1 cells, is important. In the case of viral infections, both humoral and cellular responses are fundamental to control the infection. The ability of an adjuvant to enhance not only the humoral but also the cell-mediated immune response increases the likelihood of developing long-lasting immunity. An effective adjuvant also would be useful for combination with a wide variety of antigens. The inventors have found that a glycosphingolipid, PBS-57, has the ability to stimulate both a cell-mediated and humoral immune response in vivo. In addition, PBS-57 is able to stimulate an immune response against a weak nominal antigen to produce antibodies and simultaneously provide for cell-mediated lysis of cells expressing specific surface antigens.

In one embodiment, the invention provides a method of enhancing the immunogenicity of a vaccine in a subject by co-administering PBS57 and the vaccine. As used herein, a "subject" is a mammal, e.g., a mouse, more suitably a human. "Enhancing the immunogenicity of a vaccine" refers to the ability of PBS-57 to enhance the humoral and/or cell mediated immune response of a subject to a vaccine in relation to a suitable control. For purposes of determining whether immunogenicity is enhanced relative to a control, a quantitative comparison of the signal in a sample from a subject vaccinated with antigen and PBS57 can be compared to the signal in a sample from a subject vaccinated with antigen alone. As used herein, immunogenicity may be measured by any assay used by those of skill in the art to measure the humoral or cell-mediated immune response. For example, the immunogenicity may be measured using an ELISA assay for various cytokine levels, the performance of which is routine to those skilled in the art.

In particular embodiments, the immune response is enhanced at least 25%, at least 30%, at least 50%, at least 60%, at least 65%, at least 70%, at least 75%, at least 80%, at least 85%, at least 90%, at least 95%, at least 100%, at least 150%, at least 200%, or at least 400%, relative to a suitable control. A suitable control may be a subject treated with a vaccine composition not including PBS57. Percent enhancement may be calculated using the following formula:

[(value representing subject's immune response after treatment with composition containing PBS57)−(value representing immune response of control)/(value representing subject's immune response after treatment with composition containing PBS57)]×100.

As used herein the term "co-administration" or "co-administering" refers to administration of at least the adjuvant and the vaccine concurrently, i.e., simultaneously in time, or sequentially, i.e., administration of an adjuvant, followed by administration of the vaccine. That is, after administration of the adjuvant, the vaccine can be administered substantially immediately after the adjuvant or the vaccine can be administered after an effective time period after the adjuvant; the effective time period is the amount of time given for realization of maximum benefit from the administration of the adjuvant. Alternatively, the adjuvant and vaccine may be co-formulated.

Vaccine compositions are suitably formulated to include PBS-57. "Vaccine" refers to a composition which, when administered to a subject, induces 10 cellular or humoral immune responses as described herein. Vaccine compositions may include an antigen or combinations of antigens; the antigen may be a polypeptide or carbohydrate moiety, or combinations thereof, for example, a glycoprotein. The antigen is suitably derived from an infectious agent (e.g., a pathogenic microorganism), a tumor, an endogenous molecule (e.g., a "self" 15 molecule), or, for purposes of study, a nominal antigen, such as ovalbumin (referred to herein as "Ova").

Vaccine compositions may also include killed or attenuated infectious agents. The vaccine compositions used in conjunction with the invention suitably include PBS57 and an antigen. The structure of PBS-57 is shown below:

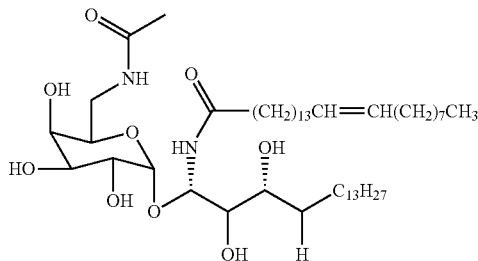

PBS57 activates NKT cells in vitro and in vivo. PBS57 contains an amide group at the C6 position of the galactose and a cis-double bond in the acyl chain of the ceramide portion. Not to be bound by theory, the double bond in the ceramide sidechain is thought to facilitate binding to the groove of the CD1d molecule and increase the solubility of glycosphingolipid. PBS57 has also been shown to induce the release of the INF-γ and IL-4 in vitro.

Vaccine compositions including PBS57 may be formulated using a variety of preparative methods and inactive ingredients known to those of skill in the art. See Remington's Pharmaceutical Sciences, Mack Publishing Co., (2000), which is incorporated herein by reference. The vaccine may also contain a suitable antigen delivery system to target the antigen to immune cells. Suitable antigen delivery systems are known in the art, and include, but are not limited to, MVA (Modified virus ankara), adenovirus, lentivirus, translocated subunit of pertussis or shiga toxin, or antigen encapuslated liposomes. Suitable effective dosage amounts of PBS57 in a vaccine compositions may be determined by those of skill in the art, but typically range from about 1 microgram to about 10,000 micrograms per kilogram of body weight, although they are typically about 1,000 micrograms or less per kilogram of body weight. In some embodiments, the effective dosage amount ranges from about 10 to about 5,000 micrograms per kilogram of body weight. In another embodiment, the effective dosage amount ranges from about 50 to about 1,000 micrograms per kilogram of body weight. In another embodiment, the effective dosage amount ranges from about 75 to about 500 micrograms per kilogram of body weight. For purposes of study, a suitable dosage for a mouse is 1 μg PBS57 per 100 μl dose. The PBS57 composition can be administered in a single dose, or may be administered in multiple doses over a period of weeks or months.

One or more antigens may be included in the compositions with PBS57, or may be formulated independently. As used herein, an antigen refers to a molecule that stimulates an immune response. It will be appreciated that the dosage of antigen will depend on the specific antigen, and on the age and immune status of the subject, as well as other relevant factors that may be determined by those skilled in the art.

Suitably, antigens are derived from attenuated or killed infectious agents. Whole microorganisms or portions thereof (e.g., membrane ghosts; crude membrane preparations, lysates and other preparations of microorganisms) may be utilized. Suitable infectious agents from which an antigen may be derived include, but are not limited to, pathogens and microorganisms such as bacteria, parasites and viruses. In some contexts, suitable antigens are obtained or derived from a viral pathogen that is associated with human disease including, but not limited to, HIV/AIDS (Retroviridae, e.g., gp120 molecules for HIV-1 and HIV-2 isolates, HTLV-I, HTLV-11), influenza viruses (Orthomyxoviridae, e.g., types A, B and C), herpes (e.g., herpes simplex viruses, HSV-1 and HSV-2 glycoproteins gB, gD and gH), rotavirus infections (Reoviridae), respiratory infections (parainfluenza and respiratory syncytial viruses), Poliomyelitis (Picornaviridae, e.g., polioviruses, rhinoviruses), measles and mumps (Paramyxoviridae), Rubella (Togaviridae, e.g., rubella virus), hepatitis (e.g., hepatitis viruses types A, B, C, D, E and/or G), cytomegalovirus (e.g., gB and gH), gastroenteritis (Caliciviridae), Yellow and West Nile fever (Flaviviridae), Rabies (Rhabdoviridae), Korean hemorrhagic fever (Bunyaviridae), Venezuelan fever (Arenaviridae), warts (Papillomavirus), simian immunodeficiency virus, encephalitis virus, varicella zoster virus, Epstein-Barr virus, and other virus families, including Coronaviridae, Birnaviridae and Filoviridae.

Suitable bacterial and parasitic antigens can also be obtained or derived from known agents responsible for diseases including, but not limited to, diphtheria, pertussis, tetanus, tuberculosis, bacterial or fungal pneumonia, otitis media, gonorrhea, cholera, typhoid, meningitis, mononucleosis, plague, shigellosis or salmonellosis, Legionnaires' disease, Lyme disease, leprosy, malaria, hookworm, Onchocerciasis, Schistosomiasis, Trypanosomiasis, Leishmaniasis, giardiases, amoebiasis, filariasis, *Borrelia*, and trichinosis. Still further antigens can be obtained or derived from unconventional pathogens such as the causative agents of kuru, Creutzfeldt-Jakob disease (CJD), scrapie, transmissible mink encephalopathy, and chronic wasting diseases, or from proteinaceous infectious particles such as prions that are associated with mad cow disease.

Additional specific pathogens from which antigens can be derived include *M. tuberculosis, Chlamydia, N. gonorrhoeae, Shigella, Salmonella, Vibrio cholerae, Treponema pallidum, Pseudomonas, Bordetella pertussis, Brucella, Francisella tularensis, Helicobacter pylori, Leptospira interrogans, Legionella pneumophila, Yersinia pestis, Streptococcus* (types A and B), pneumococcus, meningococcus, *Haemophilus influenza* (type b), *Toxoplasma gondii, Moraxella catarrhalis*, donovanosis, and actinomycosis; fungal pathogens include candidiasis and aspergillosis; parasitic pathogens include *Taenia*, flukes, roundworms, amebiasis, giardiasis, *Cryptosporidium, Schistosoma, Pneumocystis carinii*, trichomoniasis and trichinosis. The present invention can also be used to provide a suitable immune response against numerous veterinary diseases, such as foot-and-mouth diseases, coronavirus, *Pasteurella multocida, Helicobacter, Strongylus vulgaris, Actinobacillus pleuropneumonia*, Bovine Viral Diarrhea Virus (BVDV), *Klebsiella pneumoniae, E. coli*, and *Bordetella pertussis*, parapertussis and brochiseptica.

In other embodiments, antigens for inclusion in vaccine compositions that may be used in the present methods are tumor-derived antigens or autologous or allogeneic whole tumor cells. Suitably, the tumor antigen is a tumor specific antigen (TSA) or a tumor associated antigen (TAA). Several tumor antigens and their expression patterns are known in the art and can be selected based on the tumor type to be treated. Non-limiting examples of tumor antigens include cdk4 (melanoma), β-catenin (melanoma), caspase-8 (squamous cell carcinoma), MAGE-1 and MAGE-3 (melanoma, breast, glioma), tyrosinase (melanoma), surface Ig idiotype (e.g., BCR) (lymphoma), Her-2/neu (breast, ovarian), MUC-1 (breast, pancreatic) and HPV E6 and E7 (cervical carcinoma). Additional suitable tumor antigens include prostate specific antigen (PSA), sialyl Tn (STn), heat shock proteins and associated tumor peptides (e.g., gp96), ganglioside molecules (e.g., GM2, GD2, and GD3), Carcinoembryonic antigen (CEA) and MART-1.

As appreciated by skilled artisans, vaccines are suitably formulated to be compatible with the intended route of administration. Examples of suitable routes of administration include parenteral, e.g., intravenous, intradermal, subcutaneous, intramuscular, oral (e.g., inhalation), transdermal (topical), intranasal, interperitoneal, transmucosal, and rectal administration. The vaccine may also include a physiologically acceptable vehicle. A "physiologically acceptable" vehicle is any vehicle that is suitable for in vivo administration (e.g., oral, transdermal or parenteral administration) or in vitro use, i.e., cell culture. Suitable physiologically acceptable vehicles for in vivo administration include water, buffered solutions and glucose solutions, among others. Additional components of the compositions may suitably include excipients such as stabilizers, preservatives, diluents, emulsifiers or lubricants, in addition to the physiologically acceptable vehicle and the antigen. In particular, suitable excipients include, but are not limited to, Tween 20, DMSO, sucrose, L-histadine, polysorbate 20 and serum.

Another embodiment of the invention is a method of stimulating a humoral immune response to an antigen. The method includes co-administering PBS-57 and the antigen to a subject, as described above. As used herein, a "humoral immune response" is the production of antibodies by B cells, and the accessory process that accompanies it, including, but not limited to, e.g., Th2 activation and cytokine production, germinal center formation and isotype switching, affinity maturation production and memory cell generation. For purposes of determining whether a humoral immune response is activated, a quantitative comparison of the signal in a sample from a subject vaccinated with antigen and PBS57 can be compared to a sample from a subject vaccinated with antigen alone. The humoral immune response may be evaluated by measuring the effector functions of antibodies, including pathogen or toxin neutralization, classical compliment activation, and opsonin promotion of phagocytosis and pathogen elimination. The antibodies produced in response to co-administering PBS-57 and an antigen may be of any type, e.g., IgM, IgA, or IgG. The humoral immune response may be assayed by any quantitative method known in the art, e.g., ELISA, single radial immunodiffusion assay (SRID), enzyme immunoassay (EIA), or hemagglutination inhibition assay (HAI).

A further embodiment of the invention is a method of activating CD4+ T lymphocytes in a subject. As understood in the art, CD4+ T cells, or "T helper cells," are cells that recognize antigens presented by class II major histocompatability marker (MHC) on the surface of antigen presenting cells, and secrete lymphokines to stimulate both cell-mediated and antibody-mediated branches of the immune system. CD4+ T cell activation promotes lymphokine secretion, immunoglobulin isotype switching, affinity maturation of the antibody response, macrophage activation and enhanced activity of natural killer (NK) and cytotoxic T cells (CTL). Lymphokines are proteins secreted by lymphocytes that affect their own activity and/or the activity of other cells. Lymphokines include, but are not limited to, interleukins and cytokines, e.g., IL-2, IL-4, IL-5, IL-6, IL-10, IL-12, or INF-γ. For purposes of determining whether a CD4+ T lymphocytes are activated, a quantitative comparison of the signal in a sample from a subject vaccinated with antigen and PBS57 can be compared to a sample from a subject vaccinated with antigen alone. Methods to assay activation CD4+ T cells are known in the art.

Another embodiment of the invention is a method of activating CD8+ T lymphocytes in a subject. CD8+ T lymphocytes recognize antigens presented by Class I MHC molecules (present on all nucleated cells). Engagement of the MHC class I-peptide complex results in delivery of lytic granules to the target cell causing lysis of the target cell. Methods used to assay the activation of CD8+ T cells are known in the art, including but not limited to ELISPOT, ELISA, and cytotoxicity assays. As used herein, a mouse model is used to monitor the activation of CD8+ T cells using a fluorescent assay to measure cell-mediated cytotoxicity, as described in Hermans et al, 2004, *Journal of Immunologic Methods*, 285:25-40, incorporated by reference in its entirety. In this assay, mice are immunized on day 0 with the vaccine with or without PBS57. Syngeneic target cells are created by isolating splenocytes from a second set of mice and labeling the cells with two separate cell-labeling fluorescent dyes or high and low concentrations of a single fluorescent dye, e.g., CFSE or CMTMR. One set of target cells is loaded with an antigen-specific peptide while a second set of target cells is loaded with an irrelevant peptide. The two target cell populations are mixed in equal amounts and injected into immunized mice. 24 hours later, mice are sacrificed, and splenocytes and blood samples are obtained. The level of each set of target cells is analyzed by flow cytometry. Activation of CD8+ lymphocytes is determined by comparing the number of target cells in a sample vaccinated with antigen and PBS57 to the number of target cells in a sample from a subject vaccinated with antigen alone.

Other aspects of the invention will become apparent by consideration of the following non-limiting examples and accompanying drawings.

EXAMPLES

Example 1

PBS57 Activation of NKT Cells In Vitro

To determine whether PBS-57 is able to stimulate NKT cells in culture, expansion of NKT cells in culture of peripheral blood lymphocytes (PBL) was measured. PBLs were derived from two healthy donors and grown in RPMI cell culture media with 5% AB serum. Cells were plated on 12-well plates at $2 \times 10^6$ PBL/well/2 ml. Wells were treated with negative controls (0.05% Tween20 and 1% DMSO in PBS or 0.05% Tween20 and 10% DMSO in PBS) or the test adjuvants (αGalCer, PBS-20, PBS-25, or PBS-57) at a final concentration of 10 ng/ml, 100 ng/ml or 1 μg/ml. The chemical structures for control compounds αGalCer, PBS-20 and PBS25 are shown below:

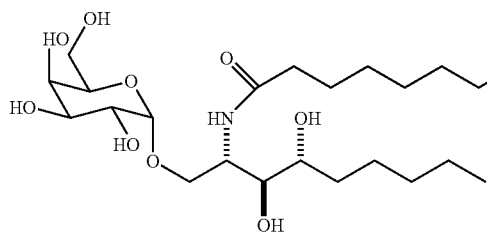

C$_{35}$H$_{77}$NO$_3$
Exact Mass: 703.58
Mol. Wt: 704.03

PBS20

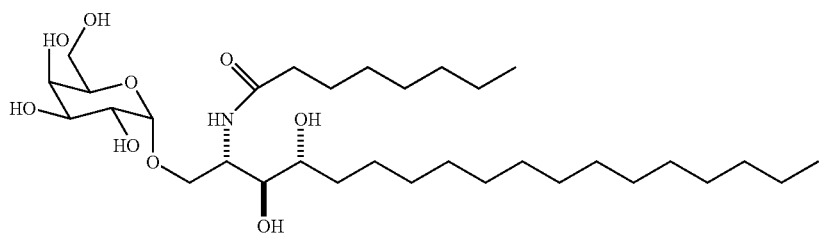

C$_{32}$H$_{63}$NO$_9$
Exact Mass: 605.45
Mol. Wt: 605.84

PBS-25

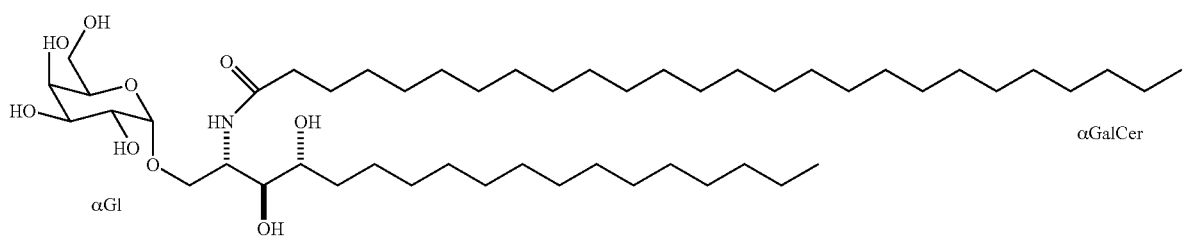

αGl

αGalCer

All cultures were supplemented with recombinant human IL2 (rhIL-2) to obtain final concentration of 100 UI/ml by day 1. All cells were cultured for 10 days at 37° C. under 5% CO$_2$. On day 7, half the culture medium (1 ml) was removed for NKT analysis. Percentage of NKT cells in the CD3+ population was detected by flow cytometry using fluorescently labeled CD1 tetramers or fluorescently labeled antibodies (anti-CD3, anti-Vβ11, and anti NKT). The NKT population was identified by flow cytometry as the Vβ11+, Tetramer+ and TCRαβ+ population. NKT cell percentage was calculated in each sample by subtracting the Vβ11+ PBS -57- tetramer+ TCRαβ+ from the Vβ11+ empty-tetramer+ TCRαβ+. FIG. 1 shows the increase of NKT cells as after treatment with PBS-57, αGalCer, PBS-25 and PBS-20. As shown, treatment of PBLs with PBS57 or αGalCer leads to an expansion of NKT cells.

In a separate experiment, the ability of PBS-57 compared to other candidate glycolipids to induce in vitro expansion of NKT cells was measured. Peripheral blood lymphocytes were derived from two healthy donors and cultured in RPMI with 5% AB serum. Cells are plated in a 12-well plate with 2×10$^6$ cells per well per 2 ml media. One well received carrier (0.05% Tween20 and 1% DMSO in PBS) as a negative control, and test wells received αGalCer, PBS-25, PBS-57, or PBS-83 at final concentrations of 1 ng/ml, 10 ng/ml and 100 ng/ml. The structure of PBS-83 is shown below:

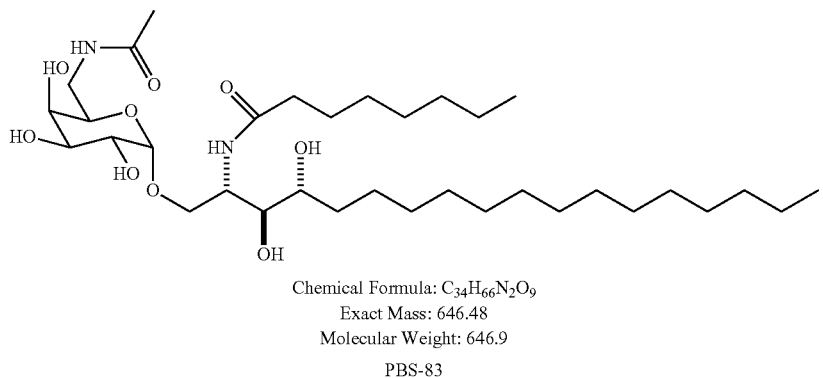 [SMILES: CCCCCCCCCCCCCC[C@@H](O)[C@@H](O)[C@H](COC1OC(CNC(C)=O)C(O)C(O)C1O)NC(=O)CCCCCCC ; "PBS-83"]

Chemical Formula: $C_{34}H_{66}N_2O_9$
Exact Mass: 646.48
Molecular Weight: 646.9
PBS-83

Figure 2:
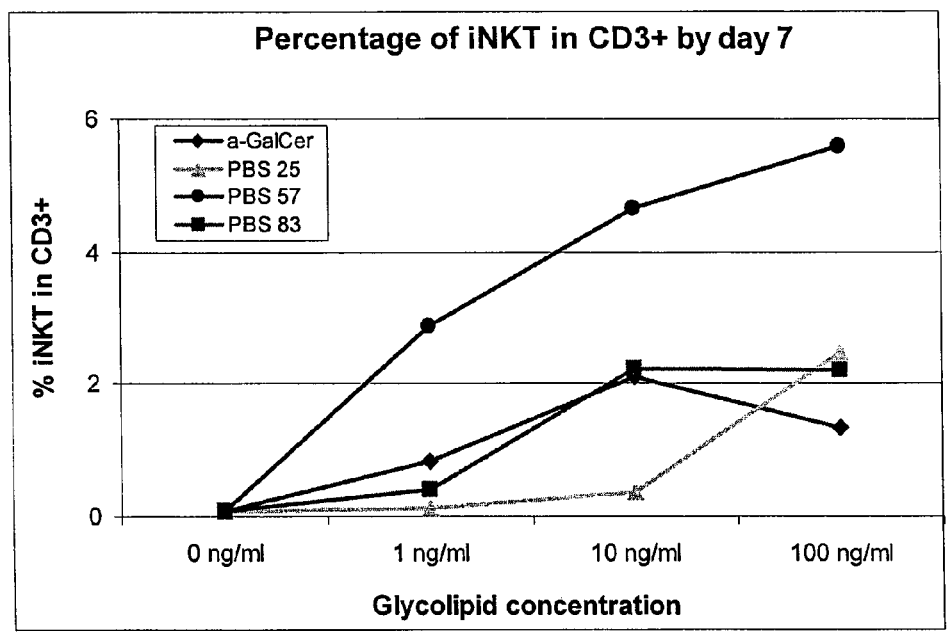
FIG. 2 is a graph showing the percentage of NKT cells on day 7 in a CD3+ T cell population of cultured PBLs treated with various amounts of αGalCer, PBS25, PBS57 and PBS83.

All cultures were supplemented with rhIL-2 to obtain a final concentration of 100 UI/ml by day 1, and cultured for 7 days at 37° C. under 5% $CO_2$ conditions. At day 7, the percentage NKT cells was detected by flow cytometry. FIG. 2 demonstrates the percentage of NKT cells on day 7 for the different glycolipid treatment conditions. Treatment with PBS57 resulted in at least a two fold increase in NKT cells over cells treated with αGalCer.

Example 2

Expansion of NKT Cells in Cultures Treated with PBS57

NKT staining was performed on a panel of fourteen healthy donor peripheral blood lymphocytes (PBL) or peripheral blood monocyte (PBMC) samples. PBLs were isolated from 12 subjects, and PBMCs were isolated from 2 subjects. Each isolated cell sample was split into two samples. The first sample from each donor was stained with 10 μl anti-Vβ11 FITC (Beckman Coulter), 10 μl anti-TCRαβ-PC5 (Beckman Coulter), and 2 μl PE-labeled PBS-57-CD1d-tetramer. The second sample from each donor was stained with 10 μl Vβ11, 10 μl anti-TCRαβ-FITC, and 2 μl PE-labeled empty-CD1d-tetramer.

Figure 3:
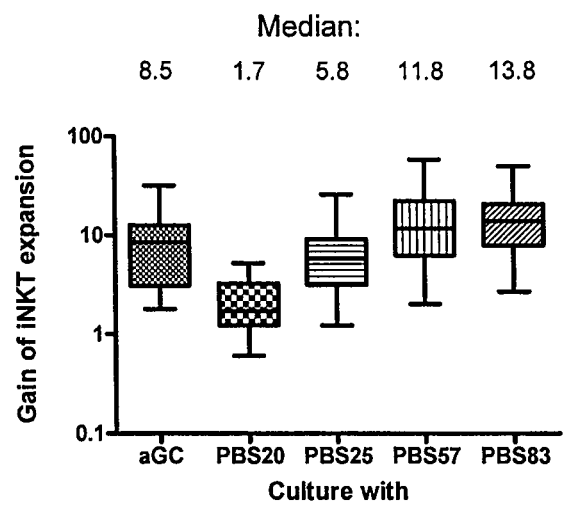
FIG. 3 is a graph showing an increase in NKT cells in in vitro cultures of PBLs isolated from volunteers treated with αGalCer, PBS20, PBS25, PBS57 and PBS83. The median value is depicted above the graphs.

To determine a percentage increase in NKT cells, the number of NKT cells on day 7 was divided by the number of NKT cells on day 0. As shown in FIG. 3, incubation with PBS57 results in a substantial increase in NKT cells in PBL cultures from human volunteers.

Example 3

Analysis of TCRαβ, NKT Cell Populations and Dendritic Cell Maturation in Mice Administered PBS-57

Figure 4:
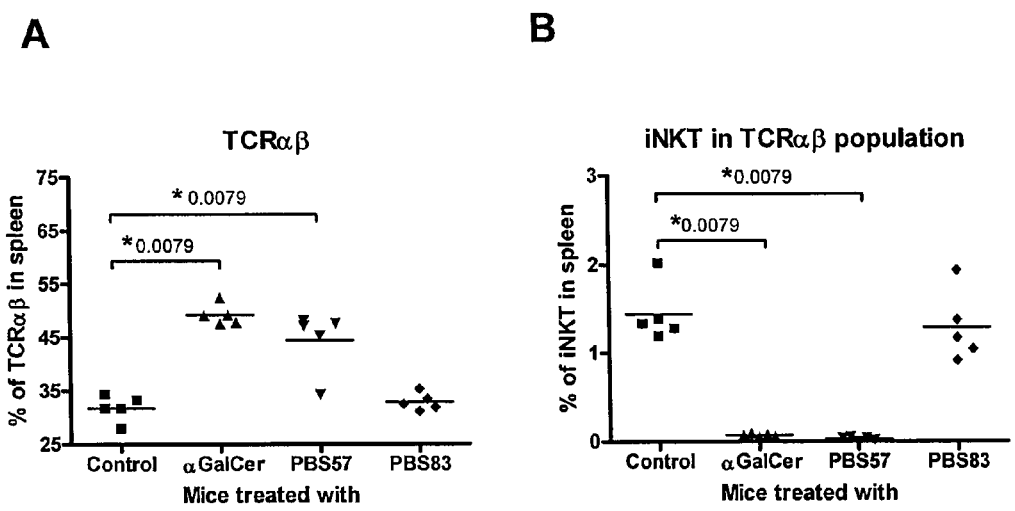
FIG. 4A is a graph depicting the percentage of TCRαβ cells within the spleen of mice 24 hours after administration of αGalCer, PBS57, and PBS83.
FIG. 4B is a graph of the percentage of NKT cells within the TCRαβ population in the spleen of mice 24 hours after administration of the adjuvant glycolipids. The two-tailed p value was calculated for each adjuvant compared to the control.

To test for adjuvant activity of PBS57 in vivo, mice were injected with test compounds and assayed for cell activation and expansion at 24 hours. Four groups of five C57B1/6J mice were each intravenously administered phosphate buffered saline (PBS) with carrier (DMSO alone), 0.97 μg of αGalCer, 1.3 μg of PBS57, or 0.97 μg of PBS83 in a total of 100 μl PBS. 24 hours after administration of the test compound, the mice were sacrificed and blood samples and splenocytes were isolated by standard methods. Percentage of NKT cells in the spleen was evaluated by flow cytometry with staining using anti-TCRαβ-FITC and PE-labeled CD1d-tetramer loaded with PBS-57 (PBS57-tetramer) or without lipid (empty-tetramer). FIG. 4A shows the increase in percentage of TCRαβ cells in mice treated with αGalCer or with PBS57 compared with control mice treated with PBS and carrier alone. The percentage of NKT cells was determined by subtracting the percentage of PBS57-tetramer+ cells from the percentage of empty-tetramer+ cells in the TCRαβ population. FIG. 4B shows the decrease in percentage of NKT cells in the spleen of mice treated with PBS57 or αGalCer relative to the control. Taken together, the result shown in FIG. 4A and FIG. 4B demonstrate that PBS57 increased the number of TCRαβ cells in the spleen of mice as effectively as αGalCer. The loss of NKT cells in the mice injected with αGalCer or PBS57 relative to control demonstrates a down-expression of TCR on the NKT cell surface.

Figure 5:
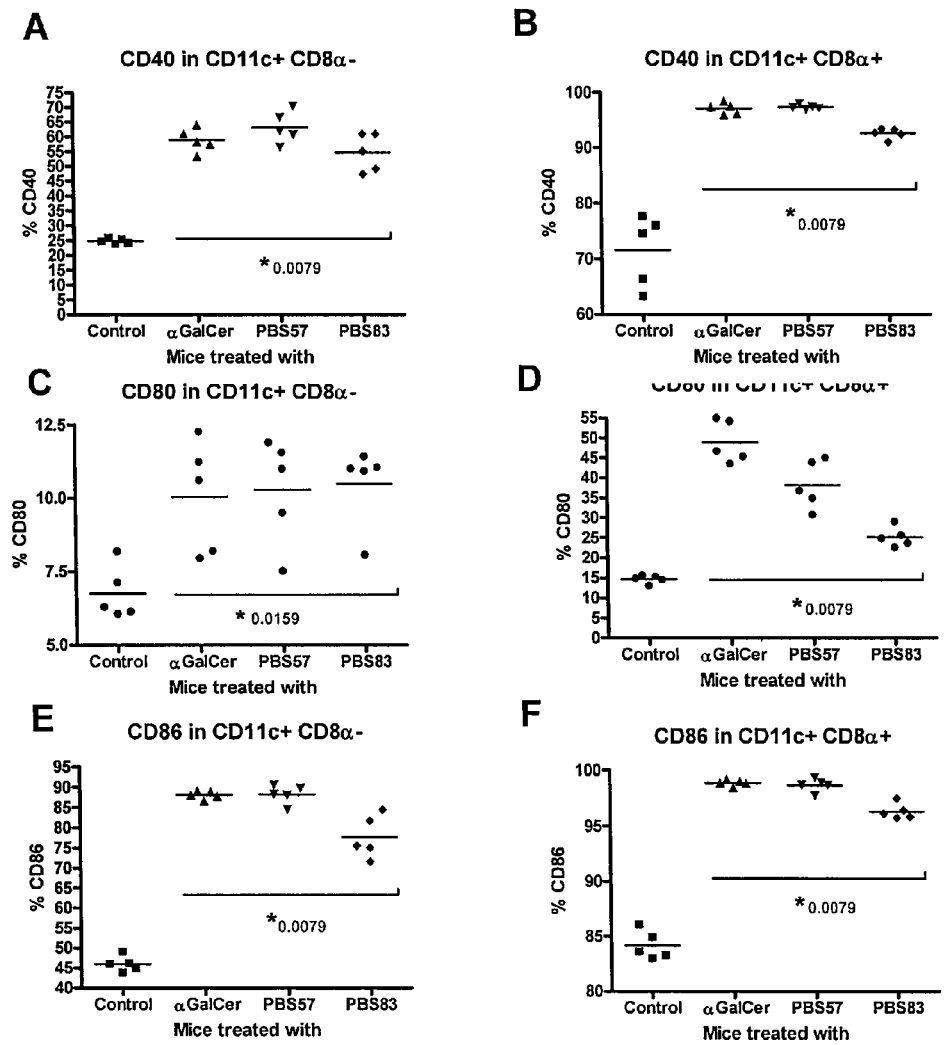
FIG. 5A is a graph of the percentage of CD40+ cells in the CD11c+ CD8α– cell population from the spleen of mice 24 hours after intravenous administration of adjuvant glycolipids.
FIG. 5B is a graph of the percentage of CD40+ cells in the CD11c+CD8α+ cell population from the spleen of mice 24 hours after intravenous administration of adjuvant glycolipids.
FIG. 5C is a graph of the percentage of CD80+ cells in the CD11c+CD8α− cell population from the spleen of mice 24 hours after intravenous administration of adjuvant glycolipids.
FIG. 5D is a graph of the percentage of CD80+ cells in the CD11c+CD8α+ cell population from the spleen of mice 24 hours after intravenous administration of adjuvant glycolipids.
FIG. 5E is a graph of the percentage of CD86+ cells in the CD11c+CD8α− cell population from the spleen of mice 24 hours after intravenous administration of adjuvant glycolipids.
FIG. 5F is a graph of the percentage of CD86+ cells in the CD11c+CD8α+ cell population from the spleen of mice 24 hours after intravenous administration of adjuvant glycolipids.

Dendritic cells (DCs) were detected in the splenocytes by flow cytometry by staining with anti-CD11c R-PE (BD Pharmingen) and anti-CD8α FITC (Beckman Coulter). Two subsets of dendritic cells, CD11c+CD8α- and CD11c+CD8α+ populations, were analyzed further. A decrease of 50% of both subsets of DCs was seen in mice treated with PBS57 or αGalCer adjuvants compared to the control. To determine if administration of glycolipid induced maturation of the two subsets of dendritic cells, the cells were stained with anti-CD40 Biotin/Stepta APC (BD Bioscience), anti-CD80 Biotin (BD Pharmingen)/Stepta APC (BD Bioscience) and anti-CD86 Biotin (BD Pharmingen)/Stepta APC (BD Bioscience) antibodies and analyzed by flow cytometry. FIGS. 5A and 5B show the percentage of CD40 positive cells in both the CD11c+CD8α- and CD11c+CD8α+ cells, respectively. FIGS. 5C and 5D shows the percentage of CD80 positive cells in both the CD11c+CD8α- and CD11c+CD8α+ cell populations, respectively. FIGS. 5E and 5F shows the percentage of CD86-positive cells in both CD11c+CD8α- and CD11c+CD8α+ cells, respectively. Horizontal lines represent the averages. Taken collectively, the data show that PBS57 and αGalCer both substantially increased the percentage of CD40+, CD80+ and CD86+ expressing cells in both the CD11c+CD8α- and CD11c+CD8α+populations.

Example 4

Protocol for Testing Adjuvanticity of PBS-57 in Mouse Model

A mouse model was used to test the in vivo specific cytotoxic T cell response (CD8+) elicited by PBS57 in combination with antigen. C57/B1/6J CD45.2 female mice were immunized on day 0 with antigen (Ovalbumin, Ova, grade VII, Sigma, St. Louis, Mo.) with or without adjuvant, adjuvant alone, or carrier alone (control) in a total of 100 μl PBS.

Figure 6:
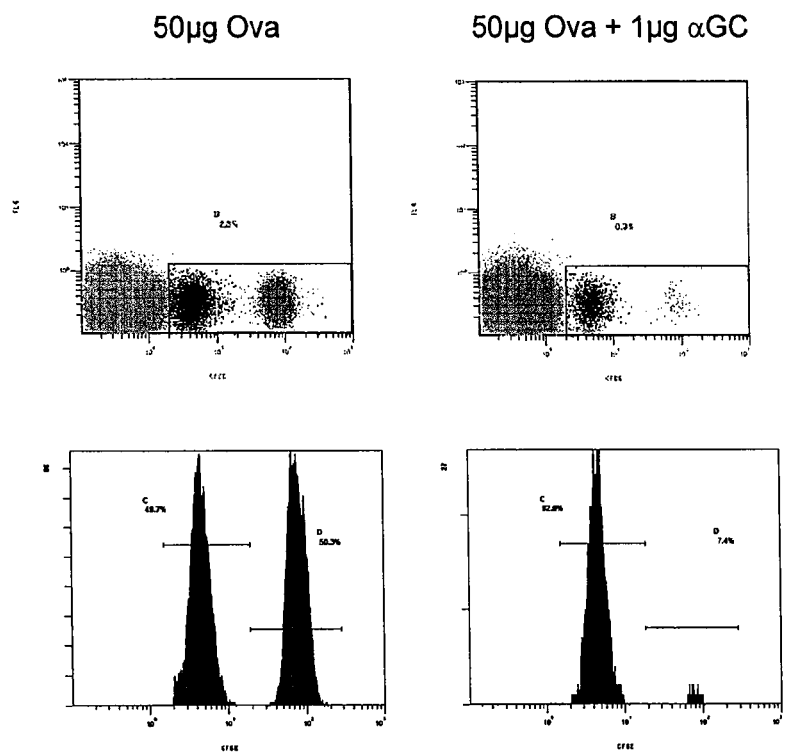
FIG. 6 is a dot plot and a histogram of results of flow cytometric CFSE staining from an assay to determine the specific lysis of antigen presenting cells for mice immunized with ovalbumin (Ova) alone or Ova and αGalCer.
Figure 7:
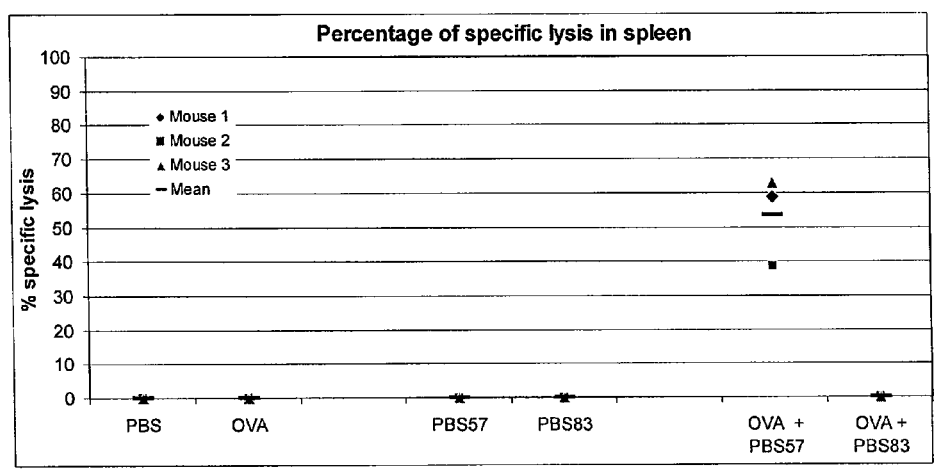
FIG. 7 is a graph depicting the percentage of specific lysis of Ova-specific target cells in the spleen of mice immunized with adjuvant, with or without Ova.

Test compounds were 1 µg PBS57, 1 µg αGalCer, 1 µg PBS83 with or without 50 µg Ova. Syngeneic target cells were prepared by isolating splenocytes from a second set of C57/B1/6J CD45.2 female mice and labeling the cells with either low concentration (0.6 µM over 10 min at 37° C.) or high concentration (6 µM over 10 minutes at 37° C.) of CFSE (fluorescent dye). The population labeled with high concentration CFSE was pre-loaded with 5 µM SIINFEKL peptide (Ova-specific peptide, NeoMPS, Inc, San Diego, Calif.) over 60 minutes at 37° C. The population labeled with low concentration CFSE was pre-loaded with 5 µl LCMV gp33-41 peptide (non-Ova peptide, NeoMPS, Inc, San Diego, Calif.) over 60 minutes at 37° C. Equal numbers of both populations of target cells were mixed ($1 \times 10^7$ cells of low or high concentration CFSE, $2 \times 10^7$ total per 100 µl) and injected intravenously into each of the immunized mice on day 10. Mice were sacrificed at day 11, and spleen cells and blood samples from the orbital sinus were collected. The mean percentage survival of the peptide-pulsed target cells (CFSE labeled) were calculated relative to the control population by flow cytometric analysis. FIG. 6B depicts typical flow cytometric data showing the loss of Ova-specific peptide loaded target cells. The cytotoxic activity was expressed as a percent specific lysis, calculated by subtracting the mean percent survival of the Ova-specific target cells from 100. FIG. 7 depicts the percentage of specific lysis of target cells in the spleen of immunized mice. Only the combination of Ova and PBS57 produced cytotoxic lysis of Ova-specific target cells in the spleen.

Example 5

Figure 8:
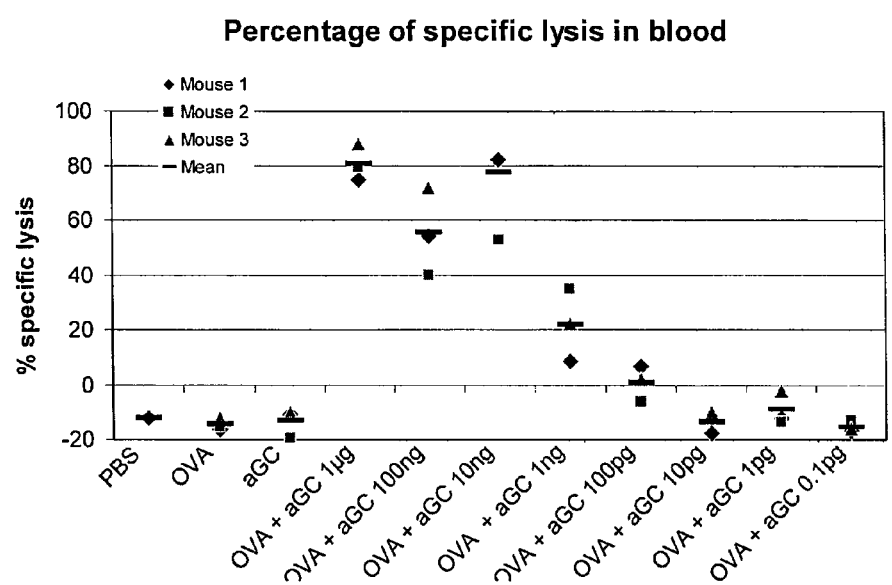
FIG. 8 is a graph depicting the percentage of specific lysis of Ova-specific target cells in the blood of mice injected intravenously ("IV") with Ova in combination with different concentrations of αGalCer.

Cytotoxic Response after Immunization with Ova with Varying Concentrations of αGalCer The in vivo cytotoxicity induced by the CD8+ T cell response to Ova-peptide loaded target cells was evaluated as described in Example 4 for varying αGalCer concentrations. Eleven groups of three mice were intravenously immunized with 100 µl total of PBS alone, 50 µg Ova alone, 1 µg of αGalCer alone, 50 µg of Ova with 1 µg, 100 ng, 10 ng, 1000 pg, 100 pg, 10 pg, or 0.1 pg αGalCer. On day 10, mice were injected intravenously with CFSE-labeled target cells. On day 11, blood samples were collected from the orbital sinus of each mouse. The mean percent survival and cytotoxic activity was determined as described above. FIG. 8 depicts the percent specific lysis for each group of mice for the specified dosages of αGalCer. The results show that αGalCer with antigen is able to generate a dose dependent specific cytotoxic effect when injected intraveneously.

Example 6

Figure 9:
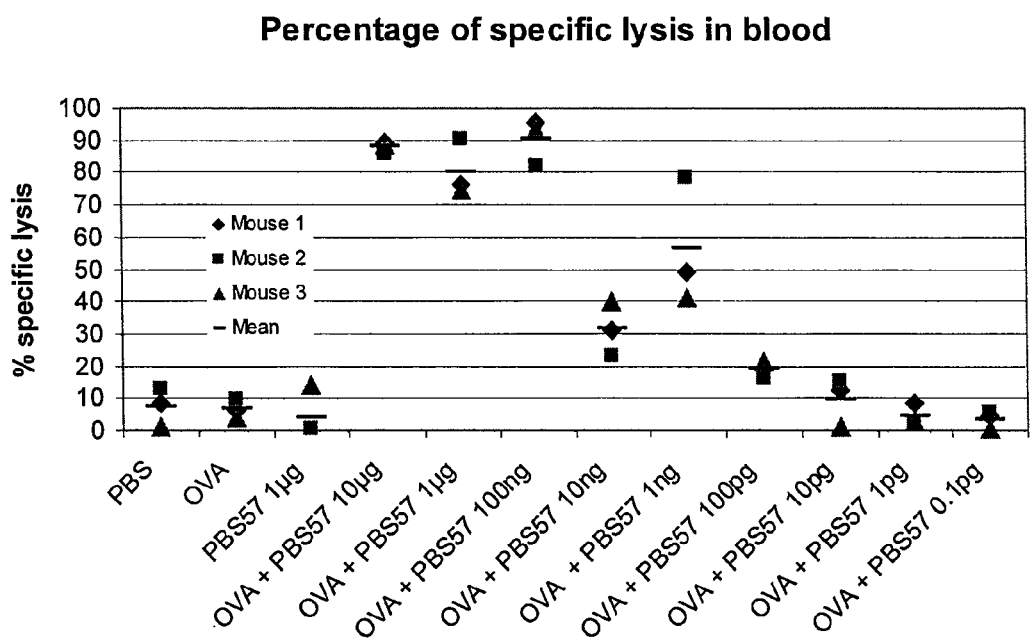
FIG. 9 is a graph depicting the percentage of specific lysis of Ova-specific target cells in the blood of mice injected IV with Ova in combination with different concentrations of PBS57.

Cytotoxic Response after Immunization with Ova with Varying Concentrations of PBS57 Intraveneously The in vivo cytotoxicity induced by CD8+ T cell response stimulated with different concentrations of PBS-57 of Ova-peptide loaded CFSE-labeled target cells was evaluated as described in Example 4. Eleven groups of three mice were intravenously immunized with 100 µl total of PBS alone, 50 µg Ova alone, 50 µg Ova with 10 µg PBS57, 1 µg PBS57, 100 ng PBS57, 10 ng PBS57, 1 ng PBS57, 100 pg PBS57, 10 pg PBS57, 1 pg PBS57, or 0.1 pg PBS57. On day 10, mice were injected intravenously with target cells, and on day 11, blood samples were collected from the orbital sinus. The mean percent survival and cytotoxic activity was determined as described above. FIG. 9 shows the percentage specific lysis in the blood for each group of mice immunized under each dosage of PBS57. The results show that PBS-57 in combination with Ova was able to induce a dose-dependent specific cytotoxic effect when injected intravenously.

Example 7

Figure 10:
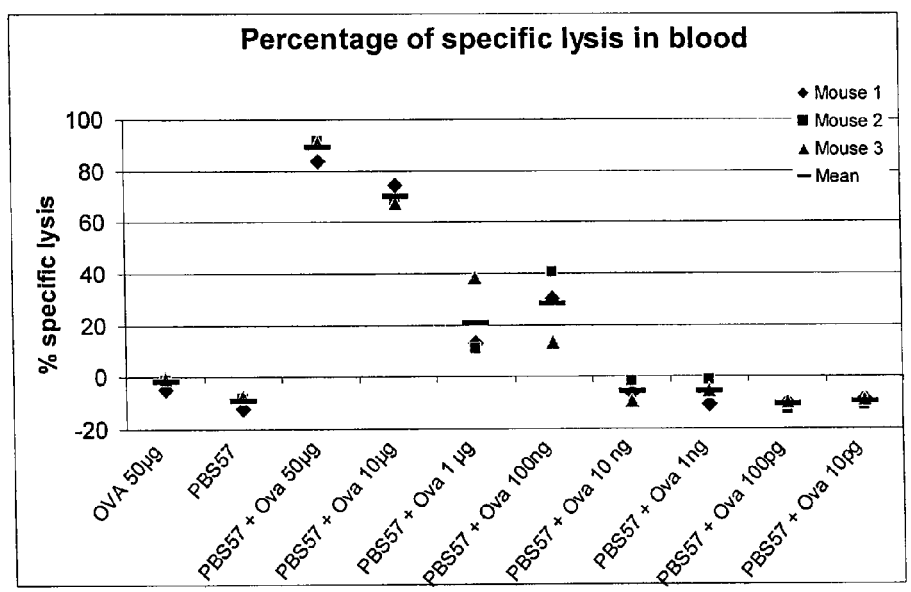
FIG. 10 is a graph depicting the percentage of specific lysis of Ova-specific target cells in the blood of mice injected IV with PBS57 in combination with different concentrations of Ova.

Cytotoxic Response after Immunization with PBS57 with Varying Concentrations of Ova Intravenously The cytotoxic response of CD8+ cells against different concentrations of ovalbumin with constant concentrations of PBS57 was evaluated as described in Example 4. Ten groups of three mice were injected intravenously on day 0 with 100 µl total in PBS of 50 µg Ova alone, 1. µg PBS57 alone, 1 µg PBS57 with 50 µg Ova, 10 µg Ova, 1 µg Ova, 100 ng Ova, 10 ng Ova, 1 ng Ova, 100 pg Ova, or 10 pg Ova. On day 10, mice were injected with target cells intravenously and on day 11, mice were sacrificed and blood samples were collected from the orbital sinus and spleen cells were isolated. The mean percentage of survival and cytotoxic activity was calculated as described above. FIG. 10 shows the percentage of specific lysis for each group of mice immunized with each dosage of Ova. The results show the cytotoxic response to vaccination with both antigen and PBS-57 is dependent on antigen concentration.

Example 8

Figure 11:
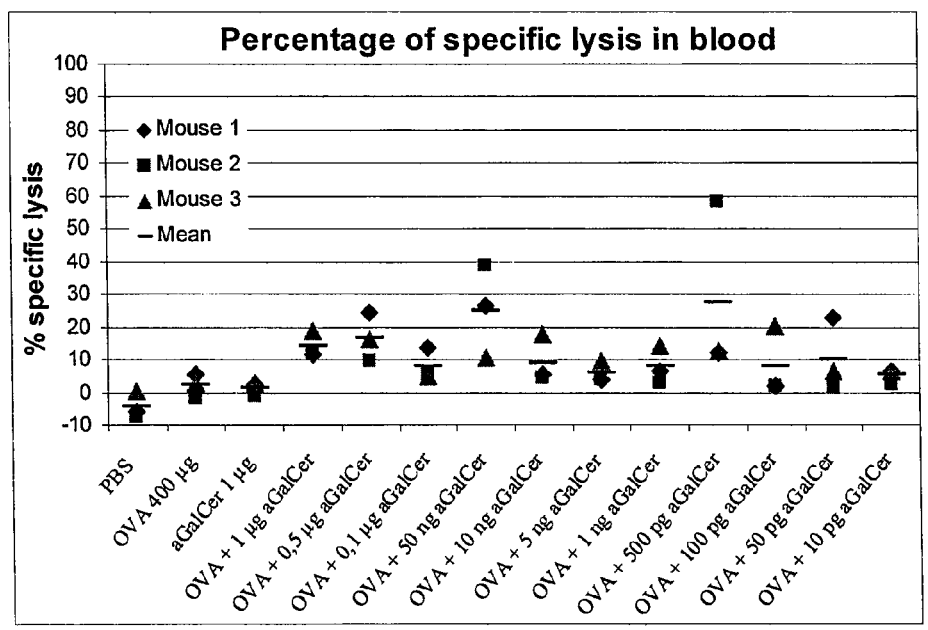
FIG. 11 is a graph depicting the percentage of specific lysis of Ova-specific target cells in the blood of mice injected intramuscularly (IM) with Ova in combination with different concentrations of αGalCer.

Cytotoxic Response after Immunization with αGalCer with Varying Concentrations of Ova Intramuscularly The cytotoxic response of CD8+ cells against different concentrations of ovalbumin with constant concentrations of αGalCer injected intramuscularly was evaluated as described in Example 4. Fourteen groups of three mice were injected intramuscularly in the hind left leg on day 0 with 100 µl total in PBS of 400 pg Ova alone, 1 µg αGalCer alone, or 400 µg Ova with 1 µg αGalCer, 0.5 µg αGalCer, 0.1 µg αGalCer, 50 ng αGalCer, 10 ng αGalCer, 5 ng αGalCer, 1 ng αGalCer, 500 pg αGalCer, 100 pg αGalCer, 50 pg αGalCer or 10 pg αGalCer. On day 10, mice were injected intraveneously with target CFSE stained cells, and on day 11 mice were sacrificed and blood samples were collected from the orbital sinus were obtained. Specific lysis of the SIINFEKL-loaded target cells was monitored by flow cytometry. The mean percent survival and cytotoxic activity was calculated as described in Example 4. FIG. 11 shows the percentage of specific lysis in the blood for each group of mice immunized under each dosage of αGalCer. The results show that αGalCer is not able to generate a specific cytotoxic T cell response when injected with the Ova antigen intramuscularly, as seen by very low specific lysis over a broad range of αGalCer concentrations from 1 µg-100 pg. These concentrations of αGalCer elicited a cytotoxic response when injected intravenously at 1 µg-10 ng, but did not elicit a cytotoxic response upon intramuscular administration.

Example 9

Figure 12:
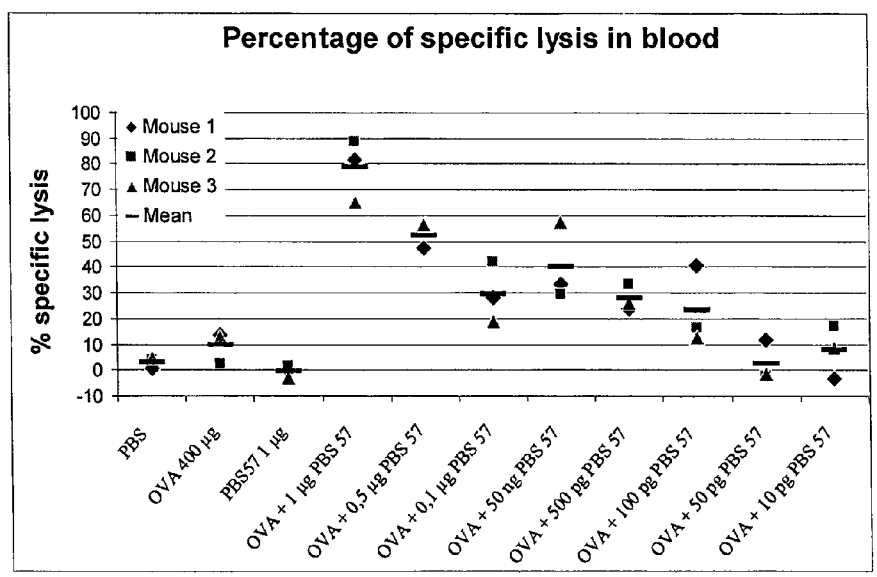
FIG. 12 is a graph depicting of the percentage of specific lysis of Ova-specific target cells in the blood of mice injected IM with Ova in combination with different concentrations of PBS57.

Cytotoxic Response after Immunization with PBS57 with Varying Concentrations of Ova Intramuscularly The cytotoxic response of CD8+ cells against intramuscular injection of PBS57 was analyzed as described in Example 4. Fourteen groups of three mice were injected intramuscularly in the hind left leg on day 0 with 100 μl total in PBS of PBS alone, 400 μg Ova alone, 1 μg PBS57 alone, or 400 μg Ova with 1 μg PBS57, 0.5 μg PBS57, 0.1 μg PBS57, 50 ng PBS57, 10 ng PBS57, 5 ng PBS57, 1 ng PBS57, 500 pg PBS57, 100 pg PBS57, 50 pg PBS57, or 10 pg PBS57. On day 10, mice were injected intravenously with target CFSE labeled cells, and blood samples from the orbital sinus on day 11. The mean percentage of survival and cytotoxic activity was determined as described in Example 4. FIG. 12 shows the specific lysis of the dosage curves of mice immunized intramuscularly with PBS57 and Ova. The results show that PBS-57 can elicit a specific cytotoxic response when injected both intravenously and intramuscularly, unlike αGalCer which can only elicit a cytotoxic response when injected intravenously.

Example 10

Comparison of the Cytotoxic Response after Intramuscular or Intravenous Immunization with Ova and PBS57 or αGalCer The cytotoxic response to Ova with PBS57 or Ova with αGalCer upon intravenous and intramuscular administration was evaluated as described in Example 4. Eight groups of mice were injected on day 0 as follows:
1) 3 mice injected IM with 400 μg Ova in 50 μl PBS;
2) 3 mice injected by IV with 400 μg Ova into 50 μl PBS;
3) 6 mice injected IM with 400 μg Ova and 1 μg αGalCer in 50 μl PBS;
4) 3 mice injected IV with 400 μg Ova and 1 μg αGalCer in 50 μl PBS;
5) 6 mice injected IM with 400 μg Ova and 1 μg αGalCer in 50 μl PBS;
6) 3 mice injected IV with 400 μg Ova and 1 μg αGalCer in 50 μl PBS;
7) 6 mice injected IM with 400 μg Ova and 1 μg PBS57 in 50 μl PBS; and
8) 3 mice injected IV with 400 μg Ova and 1 μg PBS57 into 50 μl PBS.

Figure 13:
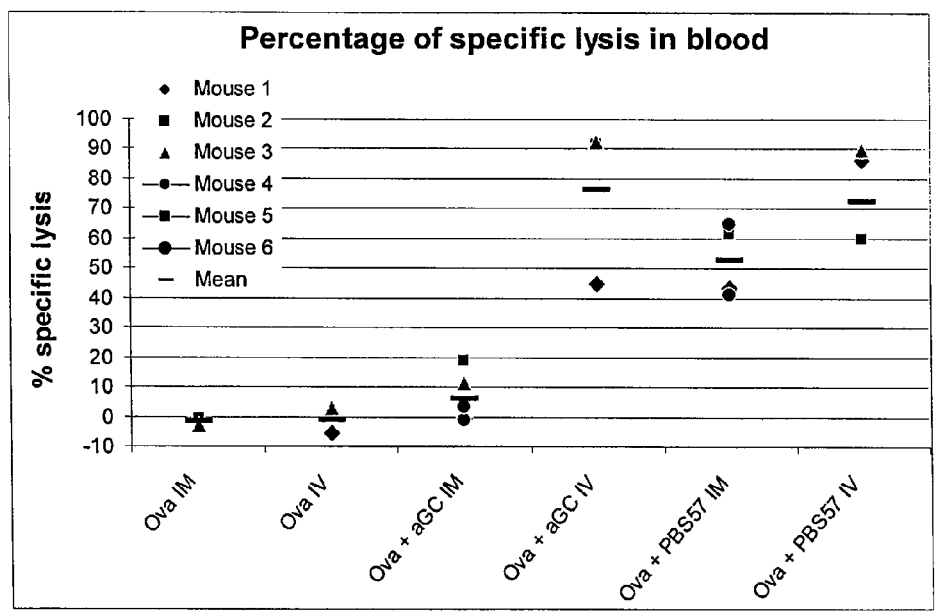
FIG. 13 is a graph comparing the percentage of specific lysis of Ova-specific target cells in the blood of mice injected either IV or IM with different Ova and adjuvant combinations.

Mice were injected with CFSE labeled target cells on day 10. Mice were sacrificed on day 11 and blood samples were collected. The mean percentage of survival and cytotoxic activity was determined as described in Example 4. FIG. 13 compares the percentage of specific lysis using different routes of administration. The results confirm that αGalCer did not induce a cytotoxic response when injected intramuscularly, while PBS57 caused a cytotoxic response regardless of the route of administration.

Example 11

PBS57 Boosts Antibody Response to Tetanus Toxoid In Vivo

Figure 14:
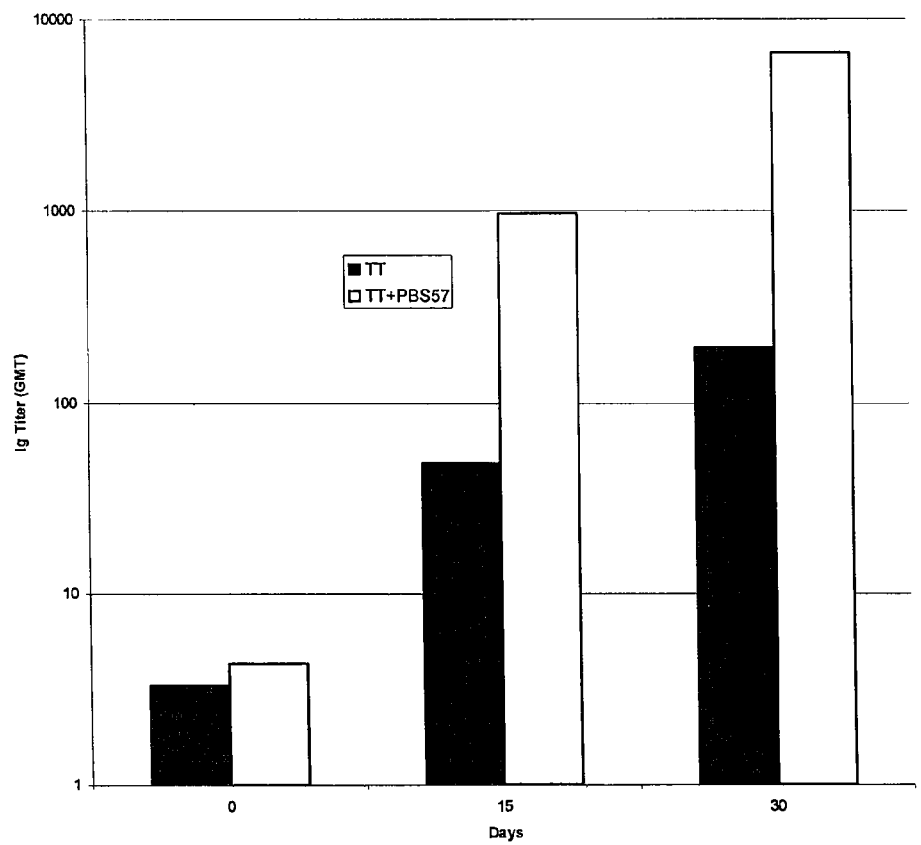
FIG. 14 is a bar graph depicting enhanced antibody production by mice immunized with a tetanus toxoid (TT) vaccine composition containing PBS-57.

To determine if the addition of PBS57 to tetanus toxoid immunization resulted in an enhanced immune response, a group of six mice were immunized intramuscularly at day 0 and day 15 with 10 μg tetanus toxoid (TT) or 10 μg tetanus toxoid in combination with 1 μg PBS57. IgG titers were determined by standard methods from blood samples drawn on day 0, 15 and 30. The antibody titer was determined by tetanus toxoid specific ELISA. As seen in FIG. 14, PBS57 enhanced the antibody response to TT.

Example 12

Comparison of the CD8+ T Cell Response after Intramuscular Immunization with Ova Alone or in Combination with PBS57

Figure 15:
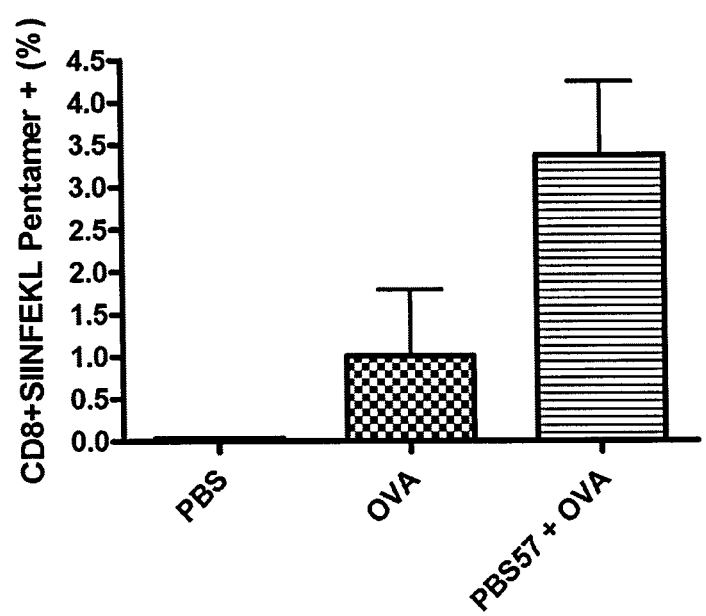
FIG. 15 is a bar graph depicting enhanced CD8+ T cell responsiveness in mice immunized intramuscularly with ovalbumin (OVA) in combination with PBS57.

A mouse model was used to test the in vivo specific T cell response (CD8+) elicited by PBS57 in combination with antigen. C57/B1/6J CD45.2 female mice were immunized intramuscularly on day 0 and 14 with antigen (Ovalbumin, Ova, grade VII, Sigma, St. Louis, Mo.) with or without adjuvant, adjuvant alone, or carrier alone (control) in a total of 100 μl PBS carrier. Test adjuvant was 1 μg PBS57 with or without 50 μg Ova. Each group included at least three mice. Blood was collected from each mouse at day 21 and isolated cells were subjected to pentamer staining with $H2K^b$-SIINFEKL pentamers after blocking the Fc receptor. FACS analysis was performed including only CD8+ cells in the analysis (CD19+ cells were excluded from the analysis to exclude any B cells). FIG. 15 depicts typical flow cytometric data showing an increase in Ova-specific CD8+ T cells after intramuscular injection with PBS57 and Ova as compared to Ova alone. The results are reported as mean+/−standard deviation of $H2K^b$-SIINFEKL specific CD8+ T cells in the blood.

Example 13

Figure 16:
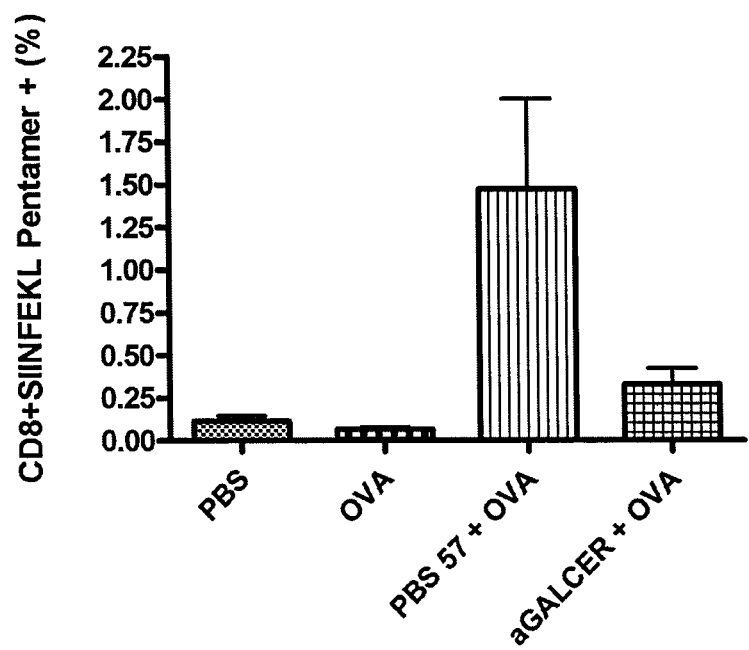
FIG. 16 is a bar graph depicting enhanced CD8+ T cell responsiveness in mice immunized subcutaneously with OVA in combination with PBS57.

Comparison of the CD8+ T Cell Response after Subcutaneous Immunization with Ova Alone or in Combination with PBS57 or αGalCer A mouse model was used to test the in vivo specific T cell response (CD8+) elicited by PBS57 in combination with antigen as compared to that of αGalCer. C57/B1/6J CD45.2 female mice were immunized subcutaneously on day 0 and 14 with antigen (Ovalbumin, Ova, grade VII, Sigma, St. Louis, Mo.) with or without adjuvant, adjuvant alone, or carrier alone (control) in a total of 100 μl PBS carrier. Test adjuvant was 1 μg PBS57 or αGalCer with or without 50 μg Ova. Each group included at least three mice. Blood was collected from each mouse at day 21 and isolated cells were subjected to pentamer staining with $H2K^b$-SIINFEKL pentamers after blocking the Fc receptor. FACS analysis was performed including only CD8+ cells in the analysis (CD19+ cells were excluded from the analysis to exclude any B cells). FIG. 16 depicts typical flow cytometric data showing an increase in Ova-specific CD8+ T cells after intramuscular injection with PBS57 and Ova as compared to Ova alone or as compared to immunization with αGalCer and Ova. The results are reported as mean+/−standard deviation of $H2K^b$-SIINFEKL specific CD8+ T cells in the blood.

While the compositions and methods of this invention have been described in terms of exemplary embodiments, it will be apparent to those skilled in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention. In addition, all patents and publications listed or described herein are incorporated in their entirety by reference.

As used in this specification and the appended claims, the singular forms "a," "an," and "the" include plural referents unless the content clearly dictates otherwise. Thus, for example, reference to a composition containing "a polynucleotide" includes a mixture of two or more polynucleotides. It should also be noted that the term "or" is generally employed in its sense including "and/or" unless the content clearly dictates otherwise. All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

It also is specifically understood that any numerical value recited herein includes all values from the lower value to the upper value, i.e., all possible combinations of numerical values between the lowest value and the highest value enumerated are to be considered to be expressly stated in this application.

I claim:

1. A method of enhancing the immunogenicity of a vaccine in a subject comprising co-administering, simultaneously or sequentially, PBS-57 and the vaccine to the subject, wherein PBS-57 is

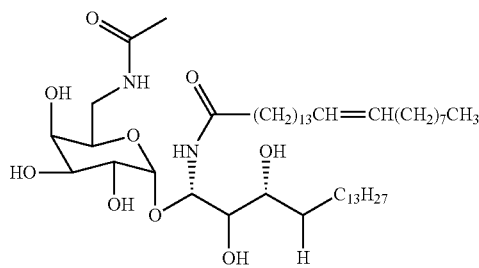

and the immunogenicity is enhanced relative to a control sample from a subject administered only the vaccine.

2. The method of claim 1, wherein the immunogenicity is enhanced at least 50% relative to the control sample.

3. The method of claim 1, wherein the immunogenicity is enhanced at least 75% relative to the control sample.

4. The method of claim 1, wherein the immunogenicity is enhanced at least 100% relative to the control sample.

5. The method of claim 1, wherein the immunogenicity is enhanced at least 150% relative to the control sample.

6. The method of claim 1, wherein the vaccine is administered intramuscularly.

7. The method of claim 1, wherein the vaccine is administered subcutaneously.

8. A method of stimulating a humoral immune response to an antigen in a subject comprising co-administering PBS-57 and a vaccine to the subject, wherein PBS-57 is

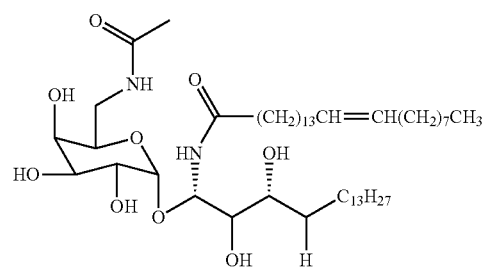

and the vaccine includes the antigen.

9. The method of claim 8, wherein the humoral immune response comprises production of IgG antibodies.

10. The method of claim 8, wherein the humoral immune response comprises production of IgA antibodies.

11. A method of activating CD4+ T lymphocytes in a subject comprising co-administering PBS-57 and a vaccine to the subject, wherein PBS-57 is

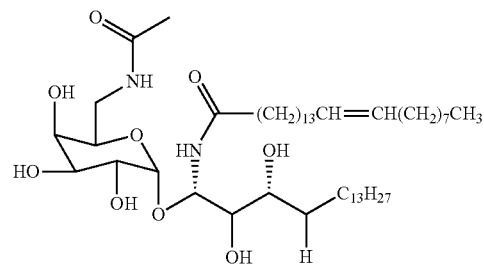

and the vaccine comprises an antigen.

12. The method of claim 11, wherein activation of the CD4+ T lymphocytes comprises an increase in a Th1 immune response.

13. The method of claim 11, wherein activation of the CD4+ T lymphocytes comprises an increase in a Th2 immune response.

14. The method of claim 11, wherein activation of the CD4+ T lymphocytes comprises an increase in a Th1 and Th2 immune response.

15. A method of activating CD8+ cytotoxic T lymphocytes in a subject comprising co-administering PBS-57 and a vaccine to the subject, wherein PBS-57 is

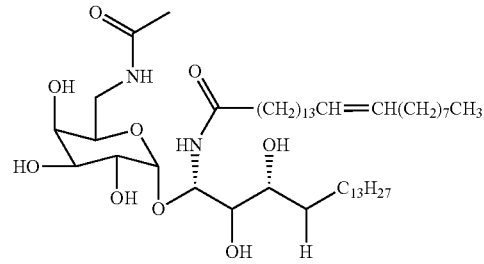

and the vaccine comprises an antigen.

16. The method of claim 15, wherein the vaccine is administered intramuscularly.

17. The method of claim 15, wherein the vaccine is administered subcutaneously.

18. The method of claim 1, wherein the vaccine is administered intravenously, intradermally, subcutaneously, intramuscularly, orally, transdermally, intranasally, interperitoneally, transmucosally or rectally.

19. The method of claim 8, wherein the vaccine is administered intravenously, intradermally, subcutaneously, intramuscularly, orally, transdermally, intranasally, interperitoneally, transmucosally or rectally.

20. The method of claim 8, wherein the humoral immune response comprises production of IgG antibodies, IgA antibodies and/or IgM antibodies.

21. The method of claim 11, wherein the vaccine is administered intravenously, intradermally, subcutaneously, intramuscularly, orally, transdermally, intranasally, interperitoneally, transmucosally or rectally.

\* \* \* \* \*